(12) United States Patent
Ohishi et al.

(10) Patent No.: US 7,662,775 B2
(45) Date of Patent: Feb. 16, 2010

(54) METHOD FOR SCREENING AGENTS FOR THE TREATMENT OF DIABETES

(75) Inventors: Takahide Ohishi, Ibaraki (JP); Jun Takasaki, Ibaraki (JP); Mitsuyuki Matsumoto, Ibaraki (JP); Tetsu Saito, Ibaraki (JP); Masazumi Kamohara, Ibaraki (JP); Takatoshi Soga, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 10/975,367

(22) Filed: Oct. 29, 2004

(65) Prior Publication Data

US 2005/0136484 A1 Jun. 23, 2005

Related U.S. Application Data

(62) Division of application No. 10/240,540, filed as application No. PCT/JP01/10472 on Nov. 30, 2001, now abandoned.

(30) Foreign Application Priority Data

Dec. 1, 2000 (JP) ............................. 2000-367349
Aug. 10, 2001 (JP) ............................. 2001-243841

(51) Int. Cl.
*A61K 38/00* (2006.01)
*A61K 51/00* (2006.01)
*C07K 1/00* (2006.01)
*C07K 14/00* (2006.01)

(52) U.S. Cl. ......................................... 514/2; 424/1.69
(58) Field of Classification Search ........................ None
See application file for complete search history.

(56) References Cited

U.S. PATENT DOCUMENTS

| | | | |
|---|---|---|---|
| 3,197,368 A | 7/1965 | Lappe et al. | |
| 6,221,660 B1 * | 4/2001 | Bonini et al. | ............... 435/348 |
| 6,468,756 B1 | 10/2002 | Bonini et al. | |
| 7,108,991 B2 | 9/2006 | Chen et al. | |
| 2003/0017528 A1 | 1/2003 | Chen et al. | |
| 2003/0139590 A1 | 7/2003 | Bonini et al. | |
| 2003/0180813 A1 | 9/2003 | Ohishi et al. | |
| 2004/0067499 A1 | 4/2004 | Haga et al. | |

FOREIGN PATENT DOCUMENTS

| | | |
|---|---|---|
| EP | 0 608 511 A2 | 8/1994 |
| EP | 1 092 727 A2 | 4/2001 |
| GB | 953899 | 4/1964 |
| WO | WO 87/01257 | 3/1987 |
| WO | WO 00/22131 | 4/2000 |
| WO | WO 00/31258 | 6/2000 |
| WO | WO 00/44382 | 8/2000 |
| WO | WO 00/50562 | 8/2000 |
| WO | WO 01/32864 A2 | 5/2001 |
| WO | WO 01/36473 A2 | 5/2001 |
| WO | WO 01/42288 A2 | 6/2001 |
| WO | WO 01/87929 A2 | 11/2001 |
| WO | WO 02/44362 A1 | 6/2002 |
| WO | WO 02/061087 A2 | 8/2002 |
| WO | WO 02/064789 A1 | 8/2002 |

OTHER PUBLICATIONS

Messer W. S. "Vasopressin and Oxytocin" [online], Apr. 3, 2000 [retrieved on Dec. 19, 2006]. Retrieved from the internet: <URL:http://www.neurosci.pharm.utoledo.edu/MBC3320/vasopressin.htm>.*
Communication enclosing a Supplementary Partial European Search Report for EPO Application No. EP 01998193, mailed Mar. 11, 2005 (7 pages).
Attwood, "The Babel of Bioinformatics," Science, 2000, 290: 471-473.
Bowie et al., "Deciphering the Message in Protein Sequences: Tolerance to Amino Acid Substitutions," Science, 1990, 247: 1306-1310.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell. Biol, 1990, 111:2129-2138.
Kuntz, "Structure-Based Strategies for Drug Design and Discovery;" Science, 1992, 257: 1078-1082.
Lazar et al., "Transforming Growth Factor α: Mutation of Aspartic Acid 47 and Leucine 48 Results in Different Biological Activities," Mol. Cell. Biol. 1998, 8:1247-1252.
Metzler et al., "Solution structure of human CTLA-4 and delineation of a CD80/CD86 binding site conserved in CD28," Nature Structural Biol., 1997, 4: 527-531.
Miller et al., "Ligand binding to proteins: The binding landscape model," Protein Science, 1997, 6: 2166-2179.
Rudinger, "1. Characteristics of the amino acids as components of a peptide hormone sequence," from *Peptide Hormones* (ed. J.A. Parsons, M.A., B.M., B.Ch.), University Park Press, Baltimore, Jun. 1976, pp. 1-7.
Skolnick et al., "From genes to protein structure and function: novel applications of computational approaches in the genomic era," Trends in Biotech., 2000, 18(1): 34-39.
Holz et al., "cAMP-dependent Mobilization of Intracellular $Ca^{2+}$ Stores by Activation of Ryanodine Receptors in Pancreatic β-Cells," J. Biological Chemistry, 274(20): 14147-14156 (1999).

(Continued)

*Primary Examiner*—Cecilia Tsang
(74) *Attorney, Agent, or Firm*—Sughrue Mion, PLLC

(57) ABSTRACT

The invention relates to a convenient screening tool for identifying an agent for treating diabetes. The screening tool is a G protein-coupled receptor, a variant of the G protein-coupled receptor, or a homolog of the G protein-coupled receptor, which promotes insulin secretion under a high glucose concentration by activation. The invention also relates to cells transformed with an expression vector comprising a polynucleotide encoding and expressing the screening tool. The invention provides a convenient screening method for identifying an agent for treating diabetes, pharmaceutical compositions comprising the agent, and a process for manufacturing the pharmaceutical composition.

4 Claims, 2 Drawing Sheets

OTHER PUBLICATIONS

Supplementary Partial European Search Report for EPO Application No. EP 01998193 mailed Jan. 3, 2005.
U.S. Appl. No. 11/657,110, Chen et al.
Fehmann, H-C et al., "Insulinotropic hormone glucagons-like peptide-I (7-37) stimulation of proinsulin gene expression and proinsulin biosynthesis in insulinoma βTC-1 cells", Endocrinology, vol. 130, No. 1, pp. 159-166, 1992.
Guo, HH et al., "Protein tolerance to amino acid change", Proc. Natl. Acad. Sci., vol. 101, No. 25, pp. 9205-9210, Jun. 22, 2004.
Non-Final Office Action dated May 16, 2007 in U.S. Appl. No. 10/511,549.
Amendment Under 37 CFR 1.111 submitted Aug. 16, 2007 in response to Non-Final Office Action dated May 16, 2007 in U.S. Appl. No. 10/511,549.
Declaration of Patent Interference No. 105,561 [U.S. Appl. No. 10/278,437 v. US Patent 7,108,991 and U.S. Appl. No. 11/657,110].
Jeanette Nilsson, et al., "cDNA cloning of human-milk bile salt-stimulated lipase and evidence for its identity to pancreatic carboxylic ester hydrase", 1990, 192, 543-550.
Applicant's response dated Mar. 9, 2007 filed in U.S. Appl. No. 10/511,549.
Fuhlendorff et al., "Stimulation of insulin release by repaglinide and glibenclamide involves both common and distinct processes." *Diabetes* 47:345-51 (1998).
International Search Report for PCT Application No. PCT/JP03/11548, mailed Oct. 21, 2003.
Kemp et al., "Synergistic effect of dimethyl sulfoxide on glucagon-like peptide 1 (GLP-1)-stimulated insulin secretion and gene transcription in INS-1 cells: characterization and implications." *Biochem. Pharmacol.* 64:689-97 (2002).
Office Action mailed Feb. 7, 2007 in U.S. Appl. No. 10/511,549.
U.S. Appl. No. 60/141,448, filed Jun. 29, 1999, Ruoping Chen.
David A. Nielsen, et al., "Control of Insulin Gene Expression in Pancreatic β-Cells and in an Insulin-producing Cell Line, RIN-5F Cells", The Journal of Biological Chemistry, 1985, 260(25):13585-13589.
Aldo Maldonato, M.D., et al., "Glucose-induced Proinsulin Biosynthesis: Role of Islet Cyclic AMP", Diabetes, 1977, 26(6):538-545.
Michael Welsh, et al., "Control of Insulin Gene Expression in Pancreatic β-Cells and in an Insulin-producing Cell Line, RIN-5F Cells", The Journal of Biological Chemistry, 1985, 260(25):13590-13594.
Peter Hammonds, et al., "Regulation and specificity of glucose-stimulated insulin gene expression in human islets of Langerhans", FEBS Letters, 1987, 223(1):131-137.
Nobuya Inagaki, et al., "c-Jun represses the human insulin promoter activity that depends on multiple cAMP response elements", Proc. Natl. Acad. Sci USA, 1992, 89:1045-1049.
Nobuya Inagaki, "Regulation of Human Insulin Gene Expression by cAMP", Molecular Genetics of Diabetes, 1994, 52(10):2528-2532.
"G Protein-Coupled Receptors and Insulin Secretion: 119 and Counting", Endocrinology, 2007, 148(6):2598-2600.
John Pickup, et al. (Eds.), Textbook of Diabetes, 1997, $2^{nd}$ Edition, vol. 1.
Stedman's Medical Dictionary, 2006, $28^{th}$ Edition.
R. Paul Robertson, et al., "G Proteins and Modulation of Insulin Secretion", Perspectives in Diabetes, 1991, 40:1-6.
Ellenberg and Rifkin's Diabetes Mellitus, 1997, $5^{th}$ Edition.
Anthony J. Weinhaus, et al., "Role of cAMP in Upregulation of Insulin Secretion During the Adaptation of Islets of Langerhans to Pregnancy", Diabetes, 1998, 47:1426-1435.
Jonathan Rachman, et al., "Normalization of Insulin Responses to Glucose by Overnight Infusion of Glucagon-Like Peptide 1 (7-36) Amide in Patients with NIDDM", Diabetes, 1996, 45:1524-1530.
Takatoshi Soga, et al., "Lysophosphatidylcholine enhances glucose-dependent insulin secretion via an orphan G-protein-coupled receptor", Biochemical and Biophysical Research Communications, 2005, 326:744-751.
Wilfred Y. Fujimoto, et al., "Phasic Effects of Glucose, Phospholipase $A_2$, and Lysophospholipids on Insulin Secretion", Endocrinology, 1987, 120:1750-1757.
Wilfred Y. Fujimoto, et al., "Phasic Effects of Glucose, p-Hydroxymercuribenzoate, and Lysophosphatidylcholine on Insulin Secretion from HIT Cells", Diabetes, 1989, 38:625-628.

* cited by examiner

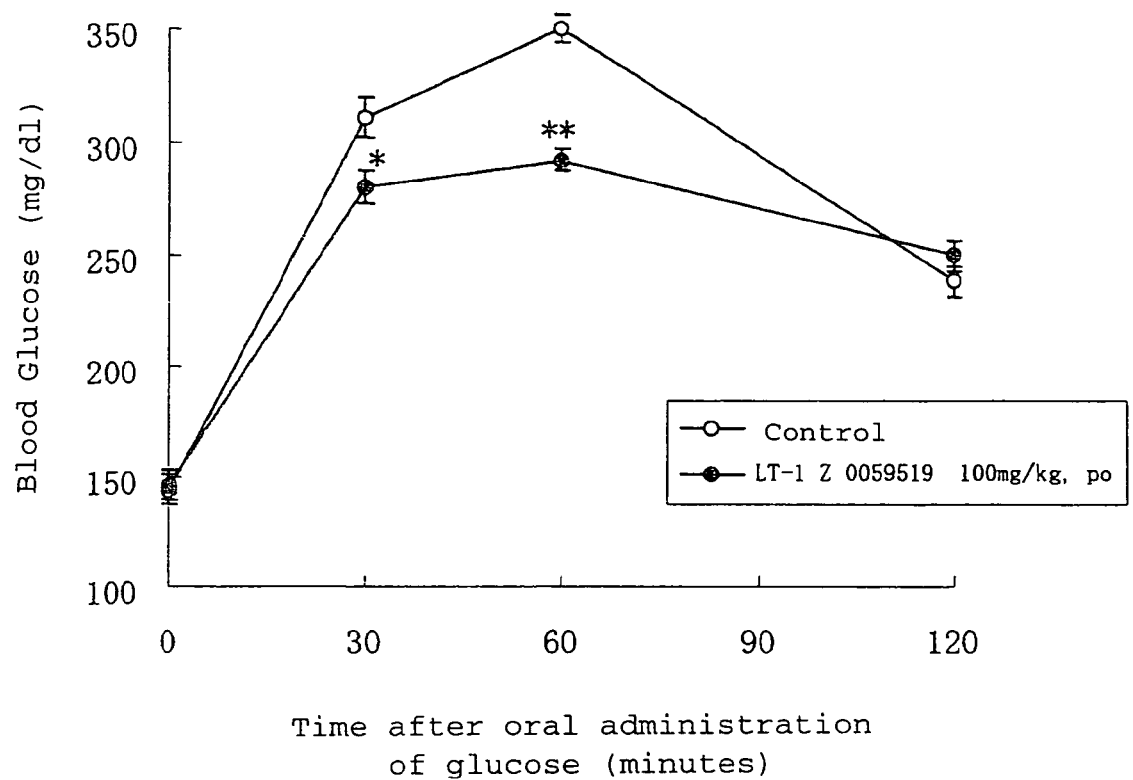

SEQUENCE LISTING

<160> NUMBER OF SEQ ID NOS: 26

<210> SEQ ID NO 1
<211> LENGTH: 1008
<212> TYPE: DNA
<213> ORGANISM: Homo sapiens
<220> FEATURE:
<221> NAME/KEY: CDS
<222> LOCATION: (1)..(1008)

<400> SEQUENCE: 1

```
atg gaa tca tct ttc tca ttt gga gtg atc ctt gct gtc ctg gcc tcc      48
Met Glu Ser Ser Phe Ser Phe Gly Val Ile Leu Ala Val Leu Ala Ser
 1               5                  10                  15 ctc atc att gct act aac aca cta gtg gct gtg gct gtg ctg ctg ttg      96
Leu Ile Ile Ala Thr Asn Thr Leu Val Ala Val Ala Val Leu Leu Leu
            20                  25                  30
```

```
atc cac aag aat gat ggt gtc agt ctc tgc ttc acc ttg aat ctg gct      144
Ile His Lys Asn Asp Gly Val Ser Leu Cys Phe Thr Leu Asn Leu Ala
         35                  40                  45 gtg gct gac acc ttg att ggt gtg gcc atc tct ggc cta ctc aca gac      192
Val Ala Asp Thr Leu Ile Gly Val Ala Ile Ser Gly Leu Leu Thr Asp
 50                  55                  60 cag ctc tcc agc cct tct cgg ccc aca cag aag acc ctg tgc agc ctg      240
Gln Leu Ser Ser Pro Ser Arg Pro Thr Gln Lys Thr Leu Cys Ser Leu
 65                  70                  75                  80 cgg atg gca ttt gtc act tcc tcc gca gct gcc tct gtc ctc acg gtc      288
Arg Met Ala Phe Val Thr Ser Ser Ala Ala Ala Ser Val Leu Thr Val
                 85                  90                  95 atg ctg atc acc ttt gac agg tac ctt gcc atc aag cag ccc ttc cgc      336
Met Leu Ile Thr Phe Asp Arg Tyr Leu Ala Ile Lys Gln Pro Phe Arg
             100                 105                 110 tac ttg aag atc atg agt ggg ttc gtg gcc ggg gcc tgc att gcc ggg      384
Tyr Leu Lys Ile Met Ser Gly Phe Val Ala Gly Ala Cys Ile Ala Gly
         115                 120                 125 ctg tgg tta gtg tct tac ctc att ggc ttc ctc cca ctc gga atc ccc      432
Leu Trp Leu Val Ser Tyr Leu Ile Gly Phe Leu Pro Leu Gly Ile Pro
130                 135                 140 atg ttc cag cag act gcc tac aaa ggg cag tgc agc ttc ttt gct gta      480
Met Phe Gln Gln Thr Ala Tyr Lys Gly Gln Cys Ser Phe Phe Ala Val
145                 150                 155                 160 ttt cac cct cac ttc gtg ctg acc ctc tcc tgc gtt ggc ttc ttc cca      528
Phe His Pro His Phe Val Leu Thr Leu Ser Cys Val Gly Phe Phe Pro
                 165                 170                 175 gcc atg ctc ctc ttt gtc ttc ttc tac tgc gac atg ctc aag att gcc      576
Ala Met Leu Leu Phe Val Phe Phe Tyr Cys Asp Met Leu Lys Ile Ala
             180                 185                 190 tcc atg cac agc cag cag att cga aag atg gaa cat gca gga gcc atg      624
Ser Met His Ser Gln Gln Ile Arg Lys Met Glu His Ala Gly Ala Met
         195                 200                 205 gct gga ggt tat cga tcc cca cgg act ccc agc gac ttc aaa gct ctc      672
Ala Gly Gly Tyr Arg Ser Pro Arg Thr Pro Ser Asp Phe Lys Ala Leu
210                 215                 220 cgt act gtg tct gtt ctc att ggg agc ttt gct cta tcc tgg acc ccc      720
Arg Thr Val Ser Val Leu Ile Gly Ser Phe Ala Leu Ser Trp Thr Pro
225                 230                 235                 240 ttc ctt atc act ggc att gtg cag gtg gcc tgc cag gag tgt cac ctc      768
Phe Leu Ile Thr Gly Ile Val Gln Val Ala Cys Gln Glu Cys His Leu
                 245                 250                 255 tac cta gtg ctg gaa cgg tac ctg tgg ctg ctc ggc gtg ggc aac tcc      816
Tyr Leu Val Leu Glu Arg Tyr Leu Trp Leu Leu Gly Val Gly Asn Ser
             260                 265                 270 ctg ctc aac cca ctc atc tat gcc tat tgg cag aag gag gtg cga ctg      864
Leu Leu Asn Pro Leu Ile Tyr Ala Tyr Trp Gln Lys Glu Val Arg Leu
         275                 280                 285 cag ctc tac cac atg gcc cta gga gtg aag aag gtg ctc acc tca ttc      912
Gln Leu Tyr His Met Ala Leu Gly Val Lys Lys Val Leu Thr Ser Phe
290                 295                 300 ctc ctc ttt ctc tcg gcc agg aat tgt ggc cca gag agg ccc agg gaa      960
Leu Leu Phe Leu Ser Ala Arg Asn Cys Gly Pro Glu Arg Pro Arg Glu
305                 310                 315                 320 agt tcc tgt cac atc gtc act atc tcc agc tca gag ttt gat ggc taa     1008
Ser Ser Cys His Ile Val Thr Ile Ser Ser Ser Glu Phe Asp Gly
                 325                 330                 335

<210> SEQ ID NO 2
<211> LENGTH: 335
```

```
<212> TYPE: PRT
<213> ORGANISM: Homo sapiens

<400> SEQUENCE: 2

Met Glu Ser Ser Phe Ser Phe Gly Val Ile Leu Ala Val Leu Ala Ser
  1               5                  10                  15

Leu Ile Ile Ala Thr Asn Thr Leu Val Ala Val Ala Val Leu Leu Leu
             20                  25                  30

Ile His Lys Asn Asp Gly Val Ser Leu Cys Phe Thr Leu Asn Leu Ala
         35                  40                  45

Val Ala Asp Thr Leu Ile Gly Val Ala Ile Ser Gly Leu Leu Thr Asp
     50                  55                  60

Gln Leu Ser Ser Pro Ser Arg Pro Thr Gln Lys Thr Leu Cys Ser Leu
 65                  70                  75                  80

Arg Met Ala Phe Val Thr Ser Ser Ala Ala Ala Ser Val Leu Thr Val
                 85                  90                  95

Met Leu Ile Thr Phe Asp Arg Tyr Leu Ala Ile Lys Gln Pro Phe Arg
            100                 105                 110

Tyr Leu Lys Ile Met Ser Gly Phe Val Ala Gly Ala Cys Ile Ala Gly
            115                 120                 125

Leu Trp Leu Val Ser Tyr Leu Ile Gly Phe Leu Pro Leu Gly Ile Pro
130                 135                 140

Met Phe Gln Gln Thr Ala Tyr Lys Gly Gln Cys Ser Phe Phe Ala Val
145                 150                 155                 160

Phe His Pro His Phe Val Leu Thr Leu Ser Cys Val Gly Phe Phe Pro
                165                 170                 175

Ala Met Leu Leu Phe Val Phe Phe Tyr Cys Asp Met Leu Lys Ile Ala
            180                 185                 190

Ser Met His Ser Gln Gln Ile Arg Lys Met Glu His Ala Gly Ala Met
            195                 200                 205

Ala Gly Gly Tyr Arg Ser Pro Arg Thr Pro Ser Asp Phe Lys Ala Leu
            210                 215                 220

Arg Thr Val Ser Val Leu Ile Gly Ser Phe Ala Leu Ser Trp Thr Pro
225                 230                 235                 240

Phe Leu Ile Thr Gly Ile Val Gln Val Ala Cys Gln Glu Cys His Leu
                245                 250                 255

Tyr Leu Val Leu Glu Arg Tyr Leu Trp Leu Leu Gly Val Gly Asn Ser
            260                 265                 270

Leu Leu Asn Pro Leu Ile Tyr Ala Tyr Trp Gln Lys Glu Val Arg Leu
            275                 280                 285

Gln Leu Tyr His Met Ala Leu Gly Val Lys Lys Val Leu Thr Ser Phe
            290                 295                 300

Leu Leu Phe Leu Ser Ala Arg Asn Cys Gly Pro Glu Arg Pro Arg Glu
305                 310                 315                 320

Ser Ser Cys His Ile Val Thr Ile Ser Ser Glu Phe Asp Gly
                325                 330                 335

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 3
```

-continued aaaatctaga atggaatcat ctttctcatt tg                                    32

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 4
cggctctaga ttagccatca aactctgagc tgg                                   33

<210> SEQ ID NO 5
<211> LENGTH: 23
<212> TYPE: DNA
<213> ORGANISM: Homo sapiens

<400> SEQUENCE: 5
gggctgcttg atggcaaggt acc                                              23

<210> SEQ ID NO 6
<211> LENGTH: 23
<212> TYPE: DNA
<213> ORGANISM: Homo sapiens

<400> SEQUENCE: 6
ctgcggagga agtgacaaat gcc                                              23

<210> SEQ ID NO 7
<211> LENGTH: 23
<212> TYPE: DNA
<213> ORGANISM: Homo sapiens

<400> SEQUENCE: 7
ggagctttgc tctatcctgg acc                                              23

<210> SEQ ID NO 8
<211> LENGTH: 23
<212> TYPE: DNA
<213> ORGANISM: Homo sapiens

<400> SEQUENCE: 8
acctctacct agtgctggaa cgg                                              23

<210> SEQ ID NO 9
<211> LENGTH: 390
<212> TYPE: DNA
<213> ORGANISM: Homo sapiens

<400> SEQUENCE: 9
ctgaggactg aaaagagagg gtgagtaatt cttcatgacc tgtaggatcc caaagatggc      60
gacctgccag cctggactgc cagcgaaggc cagaatcgtg ctgtagctct gaacccacag     120
ctcctctgcc cctggcccat gagaatttca gctggagaga tagcatgccc tggtaagtga     180
agtcctgcca cttcgagaca tggaatcatc tttctcattt ggagtgatcc ttgctgtcct     240
ggcctccctc atcattgcta ctaacacact agtggctgtg ctgtgctgc tgttgatcca     300 caagaatgat ggtgtcagtc tctgcttcac cttgaatctg gctgtggctg acaccttgat     360
tggtgtggcc atctctggcc tactcacaga                                     390

<210> SEQ ID NO 10

<211> LENGTH: 223
<212> TYPE: DNA
<213> ORGANISM: Homo sapiens

<400> SEQUENCE: 10

```
ctgtggctgc tcggcgtggg caactccctg ctcaacccac tcatctatgc ctattggcag        60
aaggaggtgc gactgcagct ctaccacatg gccctaggag tgaagaaggt gctcacctca       120
ttcctcctct ttctctcggc caggaattgt ggcccagaga ggcccaggga aagttcctgt       180
cacatcgtca ctatctccag ctcagagttt gatggctaag acg                         223
```

<210> SEQ ID NO 11
<211> LENGTH: 21
<212> TYPE: DNA
<213> ORGANISM: Homo sapiens

<400> SEQUENCE: 11

```
gttgatccac aagaatgatg g                                                  21
```

<210> SEQ ID NO 12
<211> LENGTH: 21
<212> TYPE: DNA
<213> ORGANISM: Homo sapiens

<400> SEQUENCE: 12

```
gaggcaatct tgagcatgtc g                                                  21
```

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 13

```
aaaatctaga atggagtcat ctttctcatt tgg                                     33
```

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 14

```
aaaatctaga ctagccatcg agctccggc                                          29
```

<210> SEQ ID NO 15
<211> LENGTH: 1008
<212> TYPE: DNA
<213> ORGANISM: Rattus sp.
<220> FEATURE:
<221> NAME/KEY: CDS
<222> LOCATION: (1)..(1008)

<400> SEQUENCE: 15

```
atg gag tca tct ttc tca ttt gga gtg atc ctt gct gtc ctg acc atc          48
Met Glu Ser Ser Phe Ser Phe Gly Val Ile Leu Ala Val Leu Thr Ile
 1               5                  10                  15 ctt atc att gct gtt aat gcg ctg gtg gtt gtg gct atg ctg cta tca          96
Leu Ile Ile Ala Val Asn Ala Leu Val Val Val Ala Met Leu Leu Ser
             20                  25                  30
```

```
atc tac aag aat gat ggt gtt ggc ctt tgc ttc acc tta aat ctg gcc    144
Ile Tyr Lys Asn Asp Gly Val Gly Leu Cys Phe Thr Leu Asn Leu Ala
         35                  40                  45 gtg gct gat acc ttg att ggc gtg gct att tct ggg cta gtt aca gac    192
Val Ala Asp Thr Leu Ile Gly Val Ala Ile Ser Gly Leu Val Thr Asp
 50                  55                  60 cag ctc tcc agc tct gct cag cac aca cag aag acc ttg tgt agc ctt    240
Gln Leu Ser Ser Ser Ala Gln His Thr Gln Lys Thr Leu Cys Ser Leu
 65                  70                  75                  80 cgg atg gca ttc gtc act tct tct gca gcc gcc tct gtc ctc acg gtc    288
Arg Met Ala Phe Val Thr Ser Ser Ala Ala Ala Ser Val Leu Thr Val
                 85                  90                  95 atg ctg att gcc ttt gac agg tac ctg gcc att aag cag ccc ctc cgt    336
Met Leu Ile Ala Phe Asp Arg Tyr Leu Ala Ile Lys Gln Pro Leu Arg
            100                 105                 110 tac ttc cag atc atg aat ggg ctt gta gcc gga gga tgc att gca ggg    384
Tyr Phe Gln Ile Met Asn Gly Leu Val Ala Gly Gly Cys Ile Ala Gly
        115                 120                 125 ctg tgg ttg ata tct tac ctt atc ggc ttc ctc cca ctt gga gtc tcc    432
Leu Trp Leu Ile Ser Tyr Leu Ile Gly Phe Leu Pro Leu Gly Val Ser
130                 135                 140 ata ttc cag cag acc acc tac cat ggg ccc tgc acc ttc ttt gct gtg    480
Ile Phe Gln Gln Thr Thr Tyr His Gly Pro Cys Thr Phe Phe Ala Val
145                 150                 155                 160 ttt cac cca agg ttt gtg ctg acc ctc tcc tgt gct ggc ttc ttc cca    528
Phe His Pro Arg Phe Val Leu Thr Leu Ser Cys Ala Gly Phe Phe Pro
                165                 170                 175 gct gtg ctc ctc ttt gtc ttc ttc tac tgt gac atg ctc aag att gcc    576
Ala Val Leu Leu Phe Val Phe Phe Tyr Cys Asp Met Leu Lys Ile Ala
            180                 185                 190 tct gtg cac agc cag cac atc cgg aag atg gaa cat gca gga gcc atg    624
Ser Val His Ser Gln His Ile Arg Lys Met Glu His Ala Gly Ala Met
        195                 200                 205 gtt gga gct tgc cgg ccc cca cgg cct gtc aat gac ttc aag gct gtc    672
Val Gly Ala Cys Arg Pro Pro Arg Pro Val Asn Asp Phe Lys Ala Val
    210                 215                 220 cgg act gta tct gtc ctt att ggg agc ttc acc ctg tcc tgg tct ccg    720
Arg Thr Val Ser Val Leu Ile Gly Ser Phe Thr Leu Ser Trp Ser Pro
225                 230                 235                 240 ttt ctc atc act agc att gtg cag gtg gcc tgc cac aaa tgc tgc ctc    768
Phe Leu Ile Thr Ser Ile Val Gln Val Ala Cys His Lys Cys Cys Leu
                245                 250                 255 tac caa gtg ctg gaa aaa tac ctc tgg ctc ctt gga gtt ggc aac tcc    816
Tyr Gln Val Leu Glu Lys Tyr Leu Trp Leu Leu Gly Val Gly Asn Ser
            260                 265                 270 ctg ctc aac cca ctc atc tat gcc tat tgg cag agg gag gtt cgg cag    864
Leu Leu Asn Pro Leu Ile Tyr Ala Tyr Trp Gln Arg Glu Val Arg Gln
        275                 280                 285 cag ctc tgc cac atg gcc ctg ggg gtg aag aag ttc ttt act tca atc    912
Gln Leu Cys His Met Ala Leu Gly Val Lys Lys Phe Phe Thr Ser Ile
    290                 295                 300 ttc ctc ctt ctc tcg gcc agg aat cgt ggt cca cag agg acc cga gaa    960
Phe Leu Leu Leu Ser Ala Arg Asn Arg Gly Pro Gln Arg Thr Arg Glu
305                 310                 315                 320 agc tcc tat cac atc gtc act atc agc cag ccg gag ctc gat ggc tag  1008
Ser Ser Tyr His Ile Val Thr Ile Ser Gln Pro Glu Leu Asp Gly
                325                 330                 335

<210> SEQ ID NO 16
<211> LENGTH: 335
```

```
<212> TYPE: PRT
<213> ORGANISM: Rattus sp.

<400> SEQUENCE: 16

Met Glu Ser Ser Phe Ser Phe Gly Val Ile Leu Ala Val Leu Thr Ile
 1               5                  10                  15

Leu Ile Ile Ala Val Asn Ala Leu Val Val Ala Met Leu Leu Ser
                 20                  25                  30

Ile Tyr Lys Asn Asp Gly Val Gly Leu Cys Phe Thr Leu Asn Leu Ala
             35                  40                  45

Val Ala Asp Thr Leu Ile Gly Val Ala Ile Ser Gly Leu Val Thr Asp
         50                  55                  60

Gln Leu Ser Ser Ala Gln His Thr Gln Lys Thr Leu Cys Ser Leu
 65                  70                  75                  80

Arg Met Ala Phe Val Thr Ser Ser Ala Ala Ala Ser Val Leu Thr Val
                 85                  90                  95

Met Leu Ile Ala Phe Asp Arg Tyr Leu Ala Ile Lys Gln Pro Leu Arg
             100                 105                 110

Tyr Phe Gln Ile Met Asn Gly Leu Val Ala Gly Gly Cys Ile Ala Gly
         115                 120                 125

Leu Trp Leu Ile Ser Tyr Leu Ile Gly Phe Leu Pro Leu Gly Val Ser
130                 135                 140

Ile Phe Gln Gln Thr Thr Tyr His Gly Pro Cys Thr Phe Ala Val
145                 150                 155                 160

Phe His Pro Arg Phe Val Leu Thr Leu Ser Cys Ala Gly Phe Pro
                 165                 170                 175

Ala Val Leu Leu Phe Val Phe Phe Tyr Cys Asp Met Leu Lys Ile Ala
             180                 185                 190

Ser Val His Ser Gln His Ile Arg Lys Met Glu His Ala Gly Ala Met
         195                 200                 205

Val Gly Ala Cys Arg Pro Pro Arg Pro Val Asn Asp Phe Lys Ala Val
     210                 215                 220

Arg Thr Val Ser Val Leu Ile Gly Ser Phe Thr Leu Ser Trp Ser Pro
225                 230                 235                 240

Phe Leu Ile Thr Ser Ile Val Gln Val Ala Cys His Lys Cys Cys Leu
                 245                 250                 255

Tyr Gln Val Leu Glu Lys Tyr Leu Trp Leu Leu Gly Val Gly Asn Ser
             260                 265                 270

Leu Leu Asn Pro Leu Ile Tyr Ala Tyr Trp Gln Arg Glu Val Arg Gln
         275                 280                 285

Gln Leu Cys His Met Ala Leu Gly Val Lys Lys Phe Phe Thr Ser Ile
     290                 295                 300

Phe Leu Leu Leu Ser Ala Arg Asn Arg Gly Pro Gln Arg Thr Arg Glu
305                 310                 315                 320

Ser Ser Tyr His Ile Val Thr Ile Ser Gln Pro Glu Leu Asp Gly
                 325                 330                 335

<210> SEQ ID NO 17
<211> LENGTH: 20
<212> TYPE: DNA
<213> ORGANISM: Rattus sp.

<400> SEQUENCE: 17
gtggctgata ccttgattgg                                              20
```

```
<210> SEQ ID NO 18
<211> LENGTH: 20
<212> TYPE: DNA
<213> ORGANISM: Rattus sp.

<400> SEQUENCE: 18
gcacagctgg gaagaagcca                                                20

<210> SEQ ID NO 19
<211> LENGTH: 20
<212> TYPE: DNA
<213> ORGANISM: Rattus sp.

<400> SEQUENCE: 19
gattggcgtg gctatttctg                                                20

<210> SEQ ID NO 20
<211> LENGTH: 20
<212> TYPE: DNA
<213> ORGANISM: Rattus sp.

<400> SEQUENCE: 20
ggaagaagcc agcacaggag                                                20

<210> SEQ ID NO 21
<211> LENGTH: 24
<212> TYPE: DNA
<213> ORGANISM: Rattus sp.

<400> SEQUENCE: 21
taagatatca accacagccc tgca                                           24

<210> SEQ ID NO 22
<211> LENGTH: 24
<212> TYPE: DNA
<213> ORGANISM: Rattus sp.

<400> SEQUENCE: 22
ctacaagccc attcatgatc tgga                                           24

<210> SEQ ID NO 23
<211> LENGTH: 21
<212> TYPE: DNA
<213> ORGANISM: Rattus sp.

<400> SEQUENCE: 23
ccgcctctgt cctcacggtc a                                              21

<210> SEQ ID NO 24
<211> LENGTH: 23
<212> TYPE: DNA
<213> ORGANISM: Rattus sp.

<400> SEQUENCE: 24
acaggtacct ggccattaag cag                                            23

<210> SEQ ID NO 25
<211> LENGTH: 22
<212> TYPE: DNA
<213> ORGANISM: Rattus sp.

<400> SEQUENCE: 25
tagagcacat ctaatcctgt cc                                             22
```

```
<210> SEQ ID NO 26
<211> LENGTH: 25
<212> TYPE: DNA
<213> ORGANISM: Rattus sp.

<400> SEQUENCE: 26
ttagagatga aagtcaggat ccagc                                              25
```

METHOD FOR SCREENING AGENTS FOR THE TREATMENT OF DIABETES

This is a divisional of application Ser. No. 10/240,540, filed Oct. 2, 2002 now abandoned, which is a 371 of PCT/JP01/10472, filed Nov. 30, 2001, which claims the benefit under 35 U.S.C. § 119 of Japanese Application No. 2000-367349, filed Dec. 1, 2000, and Japanese Application No. 2001-243841, filed Aug. 10, 2001, all of which are incorporated herein by reference.

TECHNICAL FIELD

The present invention relates to a method for screening agents for the treatment of diabetes.

BACKGROUND ART

Diabetes is a disease with a persistent hyperglycemia, and it is considered that many environmental factors and genetic factors cause diabetes. A main factor regulating blood glucose is insulin, and it is known that a deficiency of insulin or a redundant presence of various factors inhibiting the activities of insulin (such as genetic factors, lack of exercise, fatness, stress, or the like) cause hyperglycemia.

There are two major types of diabetes, which are classified into an insulin dependent diabetes mellitus (IDDM) caused by a decreased pancreatic insulin secretion due to an autoimmune disease or the like, and a noninsulin dependent diabetes mellitus (NIDDM) caused by a decreased pancreatic insulin secretion due to an exhausted pancreas with a continuous hypersecretion of insulin. It is considered that 95% or more of Japanese patients with diabetes are NIDDM, and there is a problem in that the number of patients increases in accordance with changes of life-style.

As the treatment of diabetes, a diet therapy, a kinesitherapy, a remedy for fatness, or the like are mainly carried out in mild cases, an oral medicament for diabetes (for example, an agent for promoting insulin secretion such as sulfonylureas) is administered when symptoms become severe, and an insulin preparation is administered in serious cases [Ryuzo Abe and Masato Kasuga, "An Approach to EBM on the Treatment of Diabetes Mellitus", Nankodo, 1997; Richard A. Harrigan et al., Annals of Emergency Medicine, 38(1), 68-78, 2001; and Japan Diabetes Society, "Tounyoubyou chiryou gaido 2000 (Treatment of diabetes mellitus, Guide 2000)", Bunkodo, 2000].

Sulfonylureas stimulate pancreatic β cells and promote insulin secretion. However, the timing of insulin secretion and an amount of insulin secreted are decided by the timing of a medicament administration and its dose, regardless of a blood glucose level. Therefore, hypoglycemia caused by a maintenance of the medicament activity, as a side effect, sometimes occurs. Further, symptoms in the digestive system such as loss of appetite occur. Furthermore, sulfonylureas are contraindicated for patients with a hepatic or renal dysfunction or severe ketosis [Richard A. Harrigan et al., Annals of Emergency Medicine, 38(1), 68-78, 2001].

The insulin preparations certainly decrease blood glucose. However, they must be administered by injection, and they sometimes cause hypoglycemia [McCrimmon R J et al., Diabete. Metab., 20(6), 503-512, 1994].

As described above, conventionally used agents for promoting insulin secretion and insulin preparations have these problems. Therefore, agents capable of a advanced control of blood glucose, i.e., agents not simply decreasing blood glucose but capable of controlling blood glucose within a normal range, are desired.

It is known that GLP-1 (Glucagon-like peptide-1), PACAP (Pituitary adenylate cyclase activating polypeptide), and GIP (Gastric inhibitory polypeptide) transduce a signal into a cell via their own specific G protein-coupled receptors, and promote insulin secretion. These G protein-coupled receptors are receptors which are coupled to a Gs protein, activate adenylate cyclase, and increase an intracellular cAMP concentration. Further, it is known that a GLP-1 receptor, a PACAP receptor, and a GIP receptor promote insulin secretion by increasing the intracellular cAMP concentration. However, it is known that the expression of these G protein-coupled receptors is distributed in pancreas but is not pancreas-specific [Dunphy J L et al., Mol. Cell. Endocrinol., 141(1-2), 179-186, 1998; Timothy James Kieffer et al., Endocrine Reviews, 20(6), 876-913, 1999; David Vaudry et al., Pharmacological Reviews, 52(2), 269-324, 2000; Jean Claude Reubi et al., Cancer Research, 60, 3105-3112, 2000; and Ted B. Usdin et al., Endocrinology, 133(6), 2861-2870, 1993], and that the activation of the GIP receptor is not effective in NIDDM (Michael A. Nauck et al., J. Clin. Invest., 91, 301-307, 1993).

In this connection, nucleotide sequences encoding the same amino acid as that of a "polypeptide having an amino acid sequence of SEQ ID NO: 2" which may be used in the present invention, and deduced amino acid sequences encoded by the nucleotide sequences are reported (WO00/22131, WO00/31258, and WO00/50562 pamphlets). However, functions of the "polypeptide having an amino acid sequence of SEQ ID NO: 2" in a body were not clearly described in these reports. For example, the polypeptide is described as a human orphan G protein-coupled receptor in the WO00/22131 and WO00/31258 pamphlets. The WO00/50562 pamphlet lists, as a use of both agonists and antagonists of the "polypeptide having an amino acid sequence of SEQ ID NO: 2", many of the same diseases with respect to both the agonists and antagonists, but does not disclose any support that the agonists or antagonists are useful for treating these diseases.

DISCLOSURE OF INVENTION

The object of the present invention is to provide a pancreas-specific polypeptide promoting insulin secretion by activation under a high glucose concentration, to provide a polynucleotide encoding the polypeptide, to provide a convenient screening system to obtain a substance useful as an agent for treating diabetes (particularly an agent for promoting insulin secretion, more particularly an agent for promoting insulin secretion specifically under a high glucose concentration) capable of controlling blood glucose within a normal range, and to provide an agent for treating diabetes containing a substance obtained by the screening system.

With the aim of solving the aforementioned problems, the present inventors have conducted intensive studies and, as a result, found that an amount of insulin secreted is increased by activation under a high glucose concentration by overexpressing a pancreas-specifically expressing "polypeptide having an amino acid sequence of SEQ ID NO: 2" in pancreatic β cells and that, by contrast, an amount of insulin secreted is not changed by activation under a low glucose concentration, and thus found that the polypeptide and the cell expressing the polypeptide may be used as a screening tool for an agent for treating diabetes having an activity promoting insulin secretion specifically under a high glucose concentration and capable of controlling blood glucose within a normal range. Further, the inventors succeeded in providing a novel screening method for an agent for treating diabetes by use of the screening tool. The inventors have confirmed that activating substances obtained by screening known compounds not known to have an activity of treating diabetes, by use of the screening method, exhibit an activity of increasing an amount of insulin and an activity of decreasing blood glucose in rat plasma when glucose is administered, and suppress an increase of a blood glucose level in a diabetes model rat when glucose is administered, and thus clarified the utility of the screening method of the present invention. Further, the inventors established a process for manufacturing a pharmaceutical composition for treating diabetes using an analysis of the polypeptide activation, and completed the present invention.

Namely, the present invention relates to:

[1] a screening tool for an agent for treating diabetes, wherein the tool is
(1) a polypeptide having an amino acid sequence of SEQ ID NO: 2 or 16, or
(2) a polypeptide having an amino acid sequence in which 1 to 10 amino acids are deleted, substituted, and/or added in an amino acid sequence of SEQ ID NO: 2 or 16, and exhibiting (a) an activity of promoting insulin secretion from pancreatic β cells by activation under a high glucose concentration and/or (b) an activity of increasing an amount of intracellular cAMP in the cells by activation;

[2] a screening tool for an agent for treating diabetes, wherein the tool is a polypeptide comprising an amino acid sequence of SEQ ID NO: 2 or 16, and exhibiting (a) an activity of promoting insulin secretion from pancreatic β cells by activation under a high glucose concentration and/or (b) an activity of increasing an amount of intracellular cAMP in the cells by activation;

[3] a screening tool for an agent for treating diabetes, wherein the tool is a polypeptide having an amino acid sequence having a 90% or more homology with an amino acid sequence of SEQ ID NO: 2 or 16, and exhibiting (a) an activity of promoting insulin secretion from pancreatic β cells by activation under a high glucose concentration and/or (b) an activity of increasing an amount of intracellular cAMP in the cells by activation;

[4] a screening tool for an agent for treating diabetes, wherein the polypeptide of the items [1] to [3] exhibits (a) an activity of promoting insulin secretion from pancreatic β cells by activation under a high glucose concentration and (b) an activity of increasing an amount of intracellular cAMP in the cells by activation;

[5] a screening tool for an agent for treating diabetes, wherein the tool is a polypeptide consisting of an amino acid sequence of SEQ ID NO: 2 or 16 (hereinafter the screening tools of the items [1] to [5] for an agent for treating diabetes are collectively referred to as "polypeptide-type screening tool for an agent for treating diabetes");

[6] a screening tool for an agent for treating diabetes, wherein the tool is a cell which is transformed with an expression vector comprising a polynucleotide encoding a polypeptide of the items [1] to [5] and expresses the polypeptide (hereinafter referred to as "transformant-type screening tool for an agent for treating diabetes");

[7] a method for screening an agent for treating diabetes, comprising the steps of:
bringing a cell of the item [6] or a cell membrane thereof into contact with a compound to be tested; and
analyzing whether or not a polypeptide of the items [1] to [5] is activated;

[8] a method for screening an agent for treating diabetes, comprising the steps of:
bringing a cell of the item [6] or a cell membrane thereof, or a polypeptide of the items [1] to [5] into contact with a compound to be tested, in the presence of a labeled agonist of a polypeptide of the items [1] to [5]; and
analyzing a change of an amount of the labeled agonist which binds to the cell, the cell membrane thereof, or the polypeptide;

[9] the screening method of the item [7] or [8], wherein the agent for treating diabetes is an agent for promoting insulin secretion;

[10] a pharmaceutical composition for treating diabetes containing a substance activating a polypeptide of the items [1] to [5];

[11] a pharmaceutical composition for treating diabetes containing a substance is obtainable by a method of the item [7] or [8];

[12] the pharmaceutical composition for treating diabetes of the item [10] or [11], which is a pharmaceutical composition for promoting insulin secretion;

[13] a process for manufacturing a pharmaceutical composition for treating diabetes, comprising the steps of:
bringing a cell of the item [6] or a cell membrane thereof into contact with a compound to be tested;
analyzing whether or not a polypeptide of the items [1] to [5] is activated; and
preparing a formulation containing the analyzed substance;

[14] a process for manufacturing a pharmaceutical composition for treating diabetes, comprising the steps of:
bringing a cell of the item [6] or a cell membrane thereof into contact with a compound to be tested, in the presence of a labeled agonist of a polypeptide of the items [1] to [5];
analyzing a change of an amount of the labeled agonist which binds to the cell or the cell membrane thereof; and
preparing a formulation containing the analyzed substance;

[15] the process for manufacturing of the item [13] or [14], wherein the pharmaceutical composition for treating diabetes is a pharmaceutical composition for promoting insulin secretion;

[16] a method for treating diabetes, comprising administering to a subject in need thereof a substance activating a polypeptide of the items [1] to [5] in an effective amount thereof;

[17] a method for promoting insulin secretion, comprising administering to a subject in need thereof a substance activating a polypeptide of the items [1] to [5] in an effective amount thereof; and

[18] use of a substance activating a polypeptide of the items [1] to [5], in the manufacture of a pharmaceutical composition for treating diabetes and/or a pharmaceutical composition for promoting insulin secretion.

The terms "agent for treating diabetes" and "pharmaceutical composition for treating diabetes" as used herein include not only a medicament for curing a diabetic patient, but also a medicament for preventing a progress of diabetes or the like.

The term "screening tool" as used herein means a tool used for screening, more particularly, a polypeptide or a cell expressing a polypeptide used for screening. The term "screening tool for an agent for treating diabetes" as used herein means a cell or a polypeptide as a subject to be brought into contact with a test compound in the method of the present invention for screening an agent for treating diabetes, for screening an agent for treating diabetes. The present invention includes use of the polypeptide of the items [1] to [5] or the cell of the item [6] in the screening of an agent for treating diabetes.

With respect to the polypeptide consisting of the amino acid sequence of SEQ ID NO: 2, the EP1092727 publication, published after the priority date of the present application, discloses a DNA sequence encoding an amino acid sequence of a polypeptide (PFI-007) consisting of the same amino acid sequence as that of SEQ ID NO: 2, and a deduced amino acid encoded by the DNA sequence, but does not disclose that the polypeptide PFI-007 was obtained. Further, the EP1092727 publication discloses treatments of various diseases as a use of substances modulating the polypeptide PFI-007, and includes a claim directed to a method for treating diabetes consisting of administering a substance modulating the polypeptide PFI-007 (an antagonist or an agonist). However, the publication does not disclose any support showing that an agonist of the polypeptide PFI-007 is effective in the treatment of diabetes, but dose disclose that an antagonist is also effective therein, and thus, apparently, the present inventors first found that the agonist is effective in the treatment of diabetes. Further, the EP1092727 publication does not disclose that an activation of the polypeptide consisting of the amino acid of SEQ ID NO:2 promotes insulin secretion, nor that the polypeptide has an activity of promoting insulin secretion from pancreatic β cells by activation in the pancreatic β cells under a high glucose concentration (hereinafter sometimes referred to as "high glucose-dependent insulin secretion promoting activity").

As mentioned above, the screening tool for an agent for treating diabetes (particularly an agent for promoting insulin secretion), the screening method for an agent for treating diabetes (particularly an agent for promoting insulin secretion), the pharmaceutical composition for treating diabetes (particularly for promoting insulin secretion), and the process for manufacturing the pharmaceutical composition described in the present application are inventions first made by the present inventors.

BRIEF DESCRIPTION OF DRAWINGS

FIG. 3 is a graph showing a time course of the blood glucose level after the oral administration of glucose in GK rats to which 2-(pyridine-4-yl)ethyl thiobenzoate (LT-1 Z 0059519) was intraperitoneally administered.

BEST MODE FOR CARRYING OUT THE INVENTION

Figure 1:
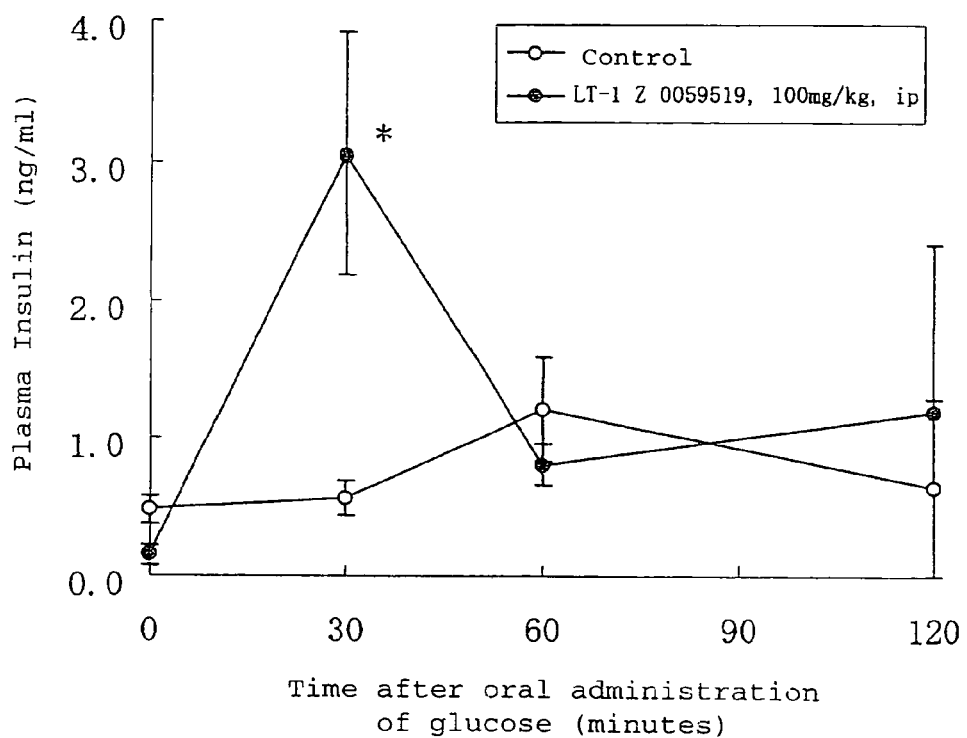
FIG. 1 is a graph showing a time course of the plasma insulin concentration after the oral administration of glucose in SD rats to which 2-(pyridine-4-yl)ethyl thiobenzoate (LT-1 Z 0059519) was intraperitoneally administered.

The present invention will be explained in detail hereinafter.

(1) The Screening Tool for an Agent for Treating Diabetes

The screening tool of the present invention for an agent for treating diabetes includes the polypeptide-type screening tool for an agent for treating diabetes and the transformant-type screening tool for an agent for treating diabetes.

1) The Polypeptide-type Screening Tool for an Agent for Treating Diabetes

As the polypeptide which may be used as the polypeptide-type screening tool of the present invention for an agent for treating diabetes, there may be mentioned, for example;
(1) a polypeptide consisting of the amino acid sequence of SEQ ID NO: 2 or 16;
(2) a polypeptide having an amino acid sequence in which one or plural amino acids are deleted, substituted, and/or added in an amino acid sequence of SEQ ID NO: 2 or 16, and exhibiting (a) an activity of promoting insulin secretion from pancreatic β cells by activation in the pancreatic β cells under a high glucose concentration and/or (b) an activity of increasing an amount of intracellular cAMP in the cells by activation in the cells (hereinafter referred to as a variation functionally equivalent); and
(3) a polypeptide having a 90% or more homology with an amino acid sequence of SEQ ID NO: 2 or 16, and exhibiting (a) an activity of promoting insulin secretion from pancreatic β cells by activation in the pancreatic β cells under a high glucose concentration and/or (b) an activity of increasing an amount of intracellular cAMP in the cells by activation in the cells (hereinafter referred to as a homologous polypeptide).

Hereinafter, these polypeptides which may be used as the polypeptide-type screening tool of the present invention for an agent for treating diabetes are collectively referred to as "polypeptides for a screening tool".

One of the polypeptides for a screening tool, the polypeptide consisting of the amino acid sequence of SEQ ID NO: 2, is a human G protein-coupled receptor consisting of 335 amino acid residues. Further, one of the polypeptides for a screening tool, the polypeptide consisting of the amino acid sequence of SEQ ID NO: 16, is a rat G protein-coupled receptor consisting of 335 amino acid residues. The homology between the human polypeptide consisting of the amino acid sequence of SEQ ID NO: 2 and the rat polypeptide consisting of the amino acid sequence of SEQ ID NO: 16 is 80.6% in the amino acid sequence comparison.

The term "homology" as used herein means a value obtained by a BLAST [Basic local alignment search tool; Altschul, S. F. et al., J. Mol. Biol., 215, 403-410,(1990)] search. The homology in the amino acid sequence may be calculated by a BLAST search algorithm. More particularly, it may be calculated using a bl2seq program (Tatiana A. Tatusova and Thomas L. Madden, FEMS Microbiol. Lett., 174, 247-250, 1999) in a BLAST package (sgi32bit edition, version 2.0.12; obtained from NCBI) in accordance with a default parameter. As a pairwise alignment parameter, a program "blastp" is used. Further, "0" as a Gap insertion cost value, "0" as a Gap elongation cost value, "SEG" as a filter for a Query sequence, and "BLOSUM62" as a Matrix are used, respectively.

The polypeptides consisting of the amino acid sequence of SEQ ID NO: 2 or 16 exhibit (a) the high glucose-dependent insulin secretion promoting activity and (b) an activity of increasing an amount of intracellular cAMP in the cells by activation in the cells (hereinafter sometimes referred to as "activity of increasing intracellular cAMP"). In this connection, the polypeptides consisting of the amino acid sequence of SEQ ID NO: 2 or 16 do not promote insulin secretion from pancreatic β cells under a low glucose concentration, when activated by overexpressing the polypeptides in the pancreatic β cells.

The term "under a high glucose concentration" as used herein means a condition in which a glucose concentration in, for example, blood or an environment around cells is higher than a normal glucose concentration range, particularly 16.8 mmol/L.

The term "under a low glucose concentration" as used herein means a condition in which the glucose concentration is lower than a normal glucose concentration range, particularly 3.3 mmol/L or less.

A method for confirming whether or not a polypeptide to be tested exhibits the "activity of promoting insulin secretion from pancreatic β cells by activation in the pancreatic β cells" as used herein is not particularly limited, but it may be confirmed by, for example, the method described below (preferably a method described in Example 5). Namely, pancreatic β cells are respectively transformed with an expression vector comprising a polynucleotide encoding the test polypeptide or a control expression vector without the polynucleotide. After a predetermined number of days (such as 2 or 3 days) from the transformation, the medium is replaced with a buffer containing a predetermined concentration of glucose. After a predetermined number of hours (such as several hours) of incubation, an amount of insulin secreted in the buffer (i.e., culture supernatant) is measured. When the amount of insulin secreted increases in the culture supernatant of the cells (test cells) transformed with the expression vector comprising the polynucleotide encoding the polypeptide, in comparison with that of the cells (control cells) transformed with the control expression vector, it may be decided that the test polypeptide exhibits the "activity of promoting insulin secretion from pancreatic β cells by activation in the pancreatic β cells". It is decided by Student's t-test whether or not the amount of insulin secreted is significantly increased in the test cells compared to the control cells. When the amount of insulin secreted increases in the test cells and the significant difference value toward the control cells is $p<0.05$ (preferably $p<0.01$), it is decided that the amount of insulin secreted has significantly increased.

A method for confirming whether or not a polypeptide to be tested exhibits the "activity of increasing an amount of intracellular cAMP by activation in cells" as used herein is not particularly limited, but it may be confirmed by, for example, the following method (preferably a method described in Example 4). More particularly, cells are respectively transformed with an expression vector comprising a polynucleotide encoding the polypeptide or a control expression vector without the polynucleotide. After a predetermined number of hours (such as 20 hours) from the transformation, the medium is replaced with a medium containing a phosphodiesterase inhibitor [such as IBMX (3-isobutyl-1-methylxanthine)]. After a predetermined number of minutes (such as 40 minutes) of incubation, an amount of cAMP in the cells is measured. When the amount of cAMP has increased in the cells transformed with the expression vector comprising the polynucleotide encoding the polypeptide, in comparison with that of the cells transformed with the control expression vector, it may be decided that the test polypeptide exhibits the "activity of increasing an amount of intracellular cAMP by activation in cells".

The state in which the polypeptide for a screening tool, a G protein-coupled receptor, is "activated" as used herein means a state in which a signal is transduced downstream of the G protein-coupled receptor regardless of a ligand binding. The polypeptide is activated when the total amount of an active form of G protein-coupled receptor exceeds a certain amount.

G protein-coupled receptors are in state of equilibrium between an active form and an inactive form. The equilibrium shifts to the active form when a ligand binds to the G protein-coupled receptor. It is known that the G protein-coupled receptor is also activated and transduces a signal downstream thereof in the absence of the ligand when the G protein-coupled receptor is overexpressed, because the total amount of the activated G protein-coupled receptor increases (Milano, C. A. et al., Science, 264, 582-586, 1994). Therefore, even if the ligand is not identified, it is possible to detect a signal from the G protein-coupled receptor by overexpressing the G protein-coupled receptor in cells. In each experiment described in Example 4 or 5, the polypeptide for a screening tool is activated in the absence of the ligand thereagainst by overexpression of polypeptide. The state is the same as that activated by an agonist binding.

The variation functionally equivalent which may be used as the polypeptide-type screening tool of the present invention for an agent for treating diabetes is not particularly limited, so long as it is a polypeptide comprising an amino acid sequence in which one or plural (preferably 1 to 10, more preferably 1 to 7, most preferably 1 to 5) such as 1 or several amino acids are deleted, substituted, and/or added at one or plural positions in the amino acid sequence of SEQ ID NO: 2 or 16, and exhibiting (a) the high glucose-dependent insulin secretion promoting activity and/or (b) the activity of increasing intracellular cAMP [preferably exhibiting both (a) the high glucose-dependent insulin secretion promoting activity and (b) the activity of increasing intracellular cAMP, more preferably in addition to these activities, (c) not promoting insulin secretion from pancreatic β cells under a low glucose concentration, when activated by overexpressing the polypeptide in the pancreatic β cells]. Further, an origin of the variation functionally equivalent is not limited to a human or a rat.

The variation functionally equivalent includes, not only human variations of the polypeptide consisting of the amino acid sequence of SEQ ID NO: 2, rat variations of the polypeptide consisting of the amino acid sequence of SEQ ID NO: 16, but also variations functionally equivalent derived from organisms other than a human or a rat (such as a mouse, a hamster, or a dog), and further polypeptides obtained by artificially modifying these native polypeptides (i.e., human or rat variations or variations functionally equivalent derived from organisms other than a human or a rat) or the polypeptide having the amino acid sequence of SEQ ID NO: 2 or 16 by genetic engineering techniques. The term "variation" as used herein means an individual difference between the same polypeptides in the same species or a difference between homologous polypeptides in several species.

Human variations of the polypeptide consisting of the amino acid sequence of SEQ ID NO: 2, rat variations of the polypeptide consisting of the amino acid sequence of SEQ ID NO: 16, or variations functionally equivalent derived from organisms other than a human or a rat may be obtained by those skilled in the art based on the information of a nucleotide sequence (for example, the nucleotide sequence of SEQ ID NO: 1) of a polynucleotide encoding the polypeptide consisting of the amino acid sequence of SEQ ID NO: 2, or that of a nucleotide sequence (for example, the nucleotide sequence of SEQ ID NO: 15) of a polynucleotide encoding the polypeptide consisting of the amino acid sequence of SEQ ID NO: 16. In this connection, genetic engineering techniques may be generally performed in accordance with known methods (for example, Maniatis, T. et al., "Molecular Cloning—A Laboratory Manual", Cold Spring Harbor Laboratory, N.Y., 1982).

For example, an appropriate probe or appropriate primers are designed in accordance with the information of a nucleotide sequence of a polynucleotide encoding the polypeptide consisting of the amino acid sequence of SEQ ID NO: 2 or 16. A polymerase chain reaction (PCR) method (Saiki, R. K. et al., Science, 239, 487-491, 1988) or a hybridization method is carried out using a sample (for example, total RNA or an mRNA fraction, a cDNA library, or a phage library) derived from an organism (for example, a mammal such as a human, a mouse, a rat, a hamster, or a dog) of interest and the primers or the probe to obtain a polynucleotide encoding the polypeptide. A desired polypeptide may be obtained by expressing the resulting polynucleotide in an appropriate expression system and confirming that the expressed polypeptide exhibits, for example, the high glucose-dependent insulin secretion promoting activity by the method described in Example 5 or the activity of increasing intracellular cAMP by the method described in Example 4.

Further, the polypeptide artificially modified by genetic engineering techniques may be obtained by, for example, the following procedure. A gene encoding the polypeptide is obtained by a conventional method such as site-specific mutagenesis (Mark, D. F. et al., Proc. Natl. Acad. Sci. USA, 81, 5662-5666, 1984). A desired polypeptide may be obtained by expressing the resulting polynucleotide in an appropriate expression system and confirming that the expressed polypeptide exhibits, for example, the high glucose-dependent insulin secretion promoting activity by the method described in Example 5 or the activity of increasing intracellular cAMP by the method described in Example 4.

Further, the variation functionally equivalent includes a polypeptide comprising an amino acid sequence of SEQ ID NO: 2 or 16, and exhibiting (a) the activity of promoting insulin secretion from pancreatic β cells by activation under a high glucose concentration and/or (b) the activity of increasing an amount of intracellular cAMP in the cells by activation. It includes, for example, a polypeptide (i.e., fusion polypeptide) in which an appropriate marker sequence or the like is added to the N-terminus and/or the C-terminus of the polypeptide consisting of the amino acid sequence of SEQ ID NO: 2 or 16, so long as the fusion polypeptide exhibits (a) the high glucose-dependent insulin secretion promoting activity and/or (b) the activity of increasing intracellular cAMP.

As the marker sequence, a sequence for easily carrying out a confirmation of polypeptide expression, a confirmation of intracellular localization thereof, a purification thereof, or the like may be used. As the sequence, there may be mentioned, for example, a FLAG epitope, a hexa-histidine tag, a hemagglutinin tag, or a myc epitope, etc.

The homologous polypeptide which may be used as the polypeptide-type screening tool of the present invention for an agent for treating diabetes is not particularly limited, so long as it is a polypeptide having an amino acid sequence having a 90% or more homology with the amino acid sequence of SEQ ID NO: 2 or 16, and exhibiting (a) the high glucose-dependent insulin secretion promoting activity and/or (b) the activity of increasing intracellular cAMP. The homologous polypeptide may have an amino acid sequence having preferably a 95% or more homology, more preferably a 98% or more homology, most preferably a 99% or more homology, with respect to the amino acid sequence of SEQ ID NO: 2 or 16.

The polypeptide for a screening tool which may be used as the polypeptide-type screening tool of the present invention for an agent for treating diabetes may be obtained by various known methods, such as known genetic engineering techniques using a polynucleotide encoding a protein of interest. More particularly, the polypeptide for a screening tool may be prepared by culturing a transformant for a screening tool described below (i.e., a transformant which is transformed with an expression vector comprising a DNA encoding the polypeptide for a screening tool and expressing the polypeptide) under a condition in which an expression of the polypeptide for a screening tool may be performed, and separating and purifying the protein of interest from the resulting culture by commonly used methods for a separation and a purification of receptor proteins.

As the polynucleotide encoding the polypeptide for a screening tool, there may be mentioned, for example, polynucleotides encoding the polypeptide consisting of the amino acid sequence of SEQ ID NO: 2, polynucleotides encoding the polypeptide consisting of the amino acid sequence of SEQ ID NO: 16, polynucleotides encoding the variations functionally equivalent, or polynucleotides encoding the homologous polypeptides. The term "polynucleotide" as used herein includes both DNA and RNA.

A method for producing the polynucleotide encoding the polypeptide for a screening tool is not particularly limited, but there may be mentioned, for example, (1) a method using PCR, (2) a method using conventional genetic engineering techniques (i.e., a method for selecting a transformant comprising a desired cDNA from strains transformed with a cDNA library), or (3) a chemical synthesis method. These methods will be explained in this order hereinafter.

In the method using PCR, the polynucleotide encoding the polypeptide for a screening tool may be produced, for example, by the following procedure.

mRNA is extracted from human cells or tissues capable of producing the polypeptide for a screening tool. A pair of primer sets, between which full-length mRNA corresponding to the polypeptide for a screening tool or a partial region of the mRNA is located, is synthesized on the basis of the nucleotide sequence of a polynucleotide encoding the polypeptide for a screening tool. Full-length cDNA encoding the polypeptide for a screening tool or a part of the cDNA may be obtained by performing a reverse transcriptase-polymerase chain reaction (RT-PCR).

More particularly, total RNA containing mRNA encoding the polypeptide for a screening tool is extracted by a known method from cells or tissues (such as pancreas) capable of producing the polypeptide for a screening tool. As an extraction method, there may be mentioned, for example, a guanidine thiocyanate-hot phenol method, a guanidine thiocyanate-guanidine hydrochloride method, or a guanidine thiocyanate-cesium chloride method. The guanidine thiocyanate-cesium chloride method is preferably used. The cells or tissue capable of producing the polypeptide for a screening tool may be identified, for example, by a northern blotting method using a polynucleotide or a part thereof encoding the polypeptide for a screening tool or a western blotting method using an antibody specific for the polypeptide for a screening tool.

Next, the extracted mRNA is purified. Purification of the mRNA may be made in accordance with a conventional method, for example, the mRNA may be purified by adsorption and elution using an oligo(dT)-cellulose column. The mRNA may be further fractionated by, for example, a sucrose density gradient centrifugation, if necessary. Alternatively, commercially available extracted and purified mRNA may be used, without carrying out the extraction of the mRNA.

Next, the first-strand cDNA is synthesized by carrying out a reverse transcriptase reaction of the purified mRNA in the presence of a random primer, an oligo dT primer, and/or a custom primer. This synthesis may be carried out in accordance with a conventional method. The resulting first-strand cDNA is subjected to PCR using two primers between which a full-length or a partial region of the polynucleotide of interest is located, thereby amplifying the cDNA of interest. The resulting DNA is fractionated by, for example, an agarose gel electrophoresis. A DNA fragment of interest may be obtained by carrying out digestion of the DNA with restriction enzymes and subsequent ligation, if necessary. Alternatively, a DNA fragment of interest may be obtained from a genomic DNA.

In the method using conventional genetic engineering techniques, the polynucleotide encoding the polypeptide for a screening tool may be produced, for example, by the following procedure.

First, single-stranded cDNA is synthesized using reverse transcriptase and, as a template, mRNA prepared by the above-mentioned PCR method, and then double-stranded cDNA is synthesized from the single-stranded cDNA. As this method, there may be mentioned, for example, an S1 nuclease method (Efstratiadis, A. et al., Cell, 7, 279-288, 1976), a Land method (Land, H. et al., Nucleic Acids Res., 9, 2251-2266, 1981), an O. Joon Yoo method (Yoo, O. J. et al., Proc. Natl. Acad. Sci. USA, 79, 1049-1053, 1983), and an Okayama-Berg method (Okayama, H. and Berg, P., Mol. Cell. Biol., 2, 161-170, 1982).

Next, a recombinant plasmid comprising the double-stranded cDNA is prepared and introduced into an *Escherichia coli* strain, such as DH 5α, thereby transforming the strain. A transformant is selected using a drug resistance against, for example, tetracycline or ampicillin as a marker. When the host cell is *E. coli*, transformation of the host cell may be carried out, for example, by the method of Hanahan (Hanahan, D. J., Mol. Biol., 166, 557-580, 1983); namely, a method in which the recombinant DNA is added to competent cells prepared in the presence of $CaCl_2$, $MgCl_2$, or RbCl. Further, as a vector other than a plasmid, a phage vector such as a lambda system may be used.

As a method for selecting a transformant containing the cDNA of interest from the resulting transformants, various methods such as (1) a screening method using a synthetic oligonucleotide probe, (2) a screening method using a probe produced by PCR, (3) a method in which screening is carried out by producing the polypeptide of interest in other animal cells, (4) a screening method using an antibody against the polypeptide for a screening tool; or (5) a method using a selective hybridization translation system, may be used.

In the screening method using a synthetic oligonucleotide probe, the transformant containing the cDNA of interest may be selected, for example, by the following procedure.

An oligonucleotide which corresponds to the whole or a part of the polypeptide for a screening tool is synthesized (in this case, it may be either a nucleotide sequence taking the codon usage into consideration or a plurality of nucleotide sequences as a combination of possible nucleotide sequences, and in the latter case, their numbers can be reduced by including inosine) and, using this oligonucleotide as a probe (labeled with $^{32}P$ or $^{33}P$), hybridized with a nitrocellulose filter on which DNAs of the transformants are denatured and fixed, to screen and select resulting positive strains.

In the screening method using a probe produced by PCR, the transformant containing the cDNA of interest may be selected, for example, by the following procedure.

Oligonucleotides of a sense primer and an antisense primer corresponding to a part of the polypeptide for a screening tool are synthesized, and a DNA fragment encoding the whole or a part of the polypeptide of interest is amplified by carrying out PCR using these primers in combination. As a template DNA used in this method, cDNA synthesized by a reverse transcription reaction from mRNA of cells capable of producing the polypeptide for a screening tool, or genomic DNA may be used. The resulting DNA fragment is labeled with $^{32}P$ or $^{33}P$, and a transformant containing the cDNA of interest is selected by carrying out a colony hybridization or a plaque hybridization using this fragment as a probe.

In the method in which screening is carried out by producing the polypeptide of interest in other animal cells, the transformant containing the cDNA of interest may be selected, for example, by the following procedure.

The polynucleotides are amplified by culturing the transformants, and animal cells are transfected with the polynucleotides (in this case, either a plasmid which can self-replicate and contains a transcription promoter region, or a plasmid which can be integrated into the chromosome of animal cells, may be used), thereby producing the polypeptides encoded by the polynucleotides on the cell surface. A transformant containing the cDNA of interest is selected from the original transformants by detecting the polypeptide for a screening tool using an antibody-against the polypeptide for a screening tool.

In the method in which the selection is carried out using an antibody against the polypeptide for a screening tool, the transformant containing the cDNA of interest may be selected, for example, by the following procedure.

First, cDNA is integrated into an expression vector, and polypeptides are produced on the cell surface of transformants. A transformant containing the cDNA of interest is selected by detecting a strain producing the desired polypeptide using an antibody against the polypeptide for a screening tool and a second antibody against the first antibody.

In the method using a selective hybridization translation system, the transformant containing the cDNA of interest may be selected, for example, by the following procedure.

First, cDNA obtained from each transformant is blotted on, for example, a nitrocellulose filter and hybridized with mRNA prepared from cells capable of producing the polypeptide for a screening tool, and then the mRNA bonded to the cDNA is dissociated and recovered. The recovered mRNA is translated into a polypeptide in an appropriate polypeptide translation system, for example, injection into Xenopus oocytes or a cell-free system such as a rabbit reticulocyte lysate or wheat germ. A transformant containing the cDNA of interest is selected by detecting it with the use of an antibody against the polypeptide for a screening tool.

A method for collecting the polynucleotide encoding the polypeptide for a screening tool from the resulting transformant of interest can be carried out in accordance with a known method (for example, Maniatis, T. et al., "Molecular Cloning—A Laboratory Manual", Cold Spring Harbor Laboratory, NY, 1982). For example, it may be carried out by separating a fraction corresponding to the plasmid DNA from cells and cutting out the cDNA region from the plasmid DNA.

In the chemical synthesis method, the polynucleotide encoding the polypeptide for a screening tool may be produced, for example, by binding DNA fragments produced by a chemical synthesis method. Each DNA can be synthesized using a DNA synthesizer [for example, Oligo 1000M DNA Synthesizer (Beckman) or 394 DNA/RNA Synthesizer (Applied Biosystems)].

Further, the polynucleotide encoding the polypeptide for a screening tool may be produced by nucleic acid chemical synthesis in accordance with a conventional method such as a phosphite triester method (Hunkapiller, M. et al., Nature, 10, 105-111, 1984), based on the information on the polypeptide for a screening tool. In this connection, codons for each amino acid are known and can be optionally selected and determined by the conventional method, for example, by taking a codon usage of each host to be used into consideration (Crantham, R. et al., Nucleic Acids Res., 9, r43-r74, 1981). Further, a partial modification of codons of these nucleotide sequences can be carried out in accordance with a conventional method, such as site specific mutagenesis which uses a primer comprised of a synthetic oligonucleotide coding for a desired modification (Mark, D. F. et al., Proc. Natl. Acad. Sci. USA, 81, 5662-5666, 1984).

Determination of the DNA sequences obtained by the above-mentioned methods can be carried out by, for example, a Maxam-Gilbert chemical modification method (Maxam, A. M. and Gilbert, W., "Methods in Enzymology", 65, 499-559, 1980) or a dideoxynucleotide chain termination method (Messing, J. and Vieira, J., Gene, 19, 269-276, 1982).

A host cell (preferably an eucaryotic cell, more preferably a 293-EBNA cell) may be transformed by re-integrating an isolated polynucleotide encoding the polypeptide for a screening tool into an appropriate vector DNA and using the resulting expression vector.

The polypeptide for a screening tool produced on the cell surface of the transformants by culturing the transformants may be separated and purified therefrom by various known separation techniques making use of the physical properties, chemical properties and the like of the polypeptide. More particularly, a cell membrane fraction containing the polypeptide for a screening tool may be obtained, for example, by culturing the cells expressing the polypeptide for a screening tool on the surface thereof, suspending the cultured cells in a buffer, homogenizing the suspension, and centrifuging the homogenate. After the resulting cell membrane fraction is solubilized, the polypeptide for a screening tool may be purified by treating the mixture with a commonly used treatment, for example, a treatment with a protein precipitant, ultrafiltration, various liquid chromatography techniques such as molecular sieve chromatography (gel filtration), adsorption chromatography, ion exchange chromatography, affinity chromatography, or high performance liquid chromatography (HPLC), or dialysis, or a combination thereof. In this connection, when the cell membrane fraction is solubilized using as mild as possible a solubilizing agent (such as CHAPS, Triton X-100, digitonin or the like), characteristics of the receptor may be maintained after the solubilization.

When the polypeptide for a screening tool is expressed as a fusion protein with a marker sequence in frame, a confirmation of the expression of the polypeptide for a screening tool, a confirmation of intracellular localization thereof, a purification thereof, or the like may be easily carried out. As the marker sequence, there may be mentioned, for example, a FLAG epitope, a hexa-histidine tag, a hemagglutinin tag, or a myc epitope. Further, by inserting a specific amino acid sequence recognized by a protease such as enterokinase, factor Xa, or thrombin between the marker sequence and the polypeptide for a screening tool, the marker sequence may be removed by the protease. For example, there is a report in which a muscarinic acetylcholine receptor and a hexa-histidine tag were connected by a thrombin recognition sequence (Hayashi, M. K. and Haga, T., J. Biochem., 120, 1232-1238, 1996).

2) The Transformant-type Screening Tool for an Agent for Treating Diabetes

As the transformant which may be used as the transformant-type screening tool of the present invention for an agent for treating diabetes (hereinafter referred to as "transformant for a screening tool"), there may be mentioned, for example;
(i) a transformant which is transformed with an expression vector comprising a polynucleotide encoding the polypeptide consisting of the amino acid sequence of SEQ ID NO: 2 or 16 and expresses the polypeptide;
(ii) a transformant which is transformed with an expression vector comprising a polynucleotide encoding a variation functionally equivalent and expresses the polypeptide; or
(iii) a transformant which is transformed with an expression vector comprising a polynucleotide encoding a homologous protein and expresses the polypeptide.

The transformant for a screening tool may be obtained, for example, by re-integrating a polynucleotide (isolated by the above-mentioned methods) encoding the polypeptide for a screening tool into an appropriate vector DNA and transforming a host cell (prefereably an eucaryotic cell, more preferably a 293-EBNA cell) with the resulting expression vector. Further, it is possible to express the polynucleotide in a desired host cell, by introducing an appropriate promoter and a sequence related to the gene expression into the vector.

The inventors enabled the polypeptide for a screening tool to be overexpressed on the cell membrane by use of an expression vector capable of adding a signal sequence at the N-terminus of the polypeptide for a screening tool. The expression vector is not particularly limited, so long as it comprises a polynucleotide encoding the polypeptide for a screening tool. As the expression vector, there may be mentioned, for example, an expression vector obtained by introducing the polynucleotide encoding the polypeptide for a screening tool into a known expression vector appropriately selected in accordance with a host cell to be used.

Further, the inventors enabled the polypeptide for a screening tool to be overexpressed on the cell membrane by use of a 293-EBNA cell. The transformant for a screening tool which may be used as the transformant-type screening tool of the present invention for an agent for treating diabetes is not particularly limited, so long as it is transformed with the expression vector, comprises the polynucleotide encoding the polypeptide for a screening tool, and expresses the polypeptide when used as the transformant-type screening tool for an agent for treating diabetes. The transformant for a screening tool may be, for example, a cell in which the polynucleotide encoding the polypeptide for a screening tool is integrated into a chromosome of a host cell, or a cell containing the polynucleotide as an expression vector comprising the polynucleotide. The transformant for a screening tool may be obtained, for example, by transforming a desired host cell with an expression vector comprising the polynucleotide encoding the polypeptide for a screening tool.

In the eucaryotic host cells, for example, cells of vertebrates, insects, and yeast are included. As the vertebral cell, there may be mentioned, for example, a COS cell as a simian cell (Gluzman, Y., Cell, 23, 175-182, 1981), a dihydrofolate reductase defective strain of a Chinese hamster ovary cell (CHO) (Urlaub, G. and Chasin, L. A., Proc. Natl. Acad. Sci. USA, 77, 4216-4220, 1980), a human embryonic kidney derived HEK293 cell, or a 293-EBNA cell (Invitrogen) obtained by introducing an EBNA-1 gene of Epstein Barr Virus.

As an expression vector for a vertebral cell, a vector containing a promoter positioned upstream of the polynucleotide to be expressed, an RNA splicing site, a polyadenylation site, a transcription termination sequence, and the like may be generally used. The vector may further contain a replication origin, if necessary. As the expression vector, there may be mentioned, for example, pSV2dhfr containing an SV40 early promoter (Subramani, S. et al., Mol. Cell. Biol., 1, 854-864, 1981), pEF-BOS containing a human elongation factor promoter (Mizushima, S. and Nagata, S., Nucleic Acids Res., 18,5322, 1990), or pCEP4 containing a cytomegalovirus promoter (Invitrogen). Further, an expression vector capable of fusing a signal sequence such as an influenza hemagglutinin signal sequence in frame to the upstream of the polypeptide to be expressed may be used (J. Biol. Chem., 267, 21995-21998, 1992). As such a vector, for example, a plasmid (a pEF-BOS signal sequence flag plasmid) obtained by introducing a sequence encoding a signal sequence and a FLAG epitope into pEF-BOS may be used.

When the 293-EBNA cell is used as the host cell, for example, pCEP4 (Invitrogen) containing a replication origin of Epstein Barr Virus and capable of performing an autonomous replication in the 293-EBNA cell may be used as the expression vector.

When the COS cell is used as the host cell, a vector having an SV40 replication origin, can perform an autonomous replication in the COS cell, and having a transcription promoter, a transcription termination signal, and an RNA splicing site, may be used as the expression vector. As the vector, there may be mentioned, for example, pME18S (Maruyama, K. and Takebe, Y., Med. Immunol., 20, 27-32, 1990), pEF-BOS (Mizushima, S. and Nagata, S., Nucleic Acids Res., 18, 5322, 1990), or pCDM8 (Seed, B., Nature, 329, 840-842, 1987).

The expression vector may be incorporated into COS cells by, for example, a DEAE-dextran method (Luthman, H. and Magnusson, G., Nucleic Acids Res., 11, 1295-1308, 1983), a calcium phosphate-DNA co-precipitation method (Graham, F. L. and van der Ed, A. J., Virology, 52, 456-457, 1973), a method using a commercially available transfection reagent (for example, FuGENE™6 Transfection Reagent; Roche Diagnostics), or an electroporation method (Neumann, E. et al., EMBO J., 1, 841-845, 1982).

When the CHO cell is used as the host cell, a transformant capable of stably producing the polypeptide for a screening tool can be obtained by carrying out a co-transfection of an expression vector comprising the polynucleotide encoding the polypeptide for a screening tool, together with a vector capable of expressing a neo gene which functions as a G418 resistance marker, such as pRSVneo (Sambrook, J. et al., "Molecular Cloning—A Laboratory Manual", Cold Spring Harbor Laboratory, NY, 1989) or pSV2-neo (Southern, P. J. and Berg, P., J. Mol. Appl. Genet., 1, 327-341, 1982), and selecting a G418 resistant colony.

The transformant for a screening tool may be cultured in accordance with the conventional method, and the polypeptide for a screening tool is produced on the cell surface. As a medium to be used in the culturing, a medium commonly used in a desired host cell may be appropriately selected. In the case of the COS cell, for example, a medium such as an RPMI-1640 medium or a Dulbecco's modified Eagle's minimum essential medium (DMEM) may be used, by supplementing it with a serum component such as fetal bovine serum (FBS) if necessary. In the case of the 293-EBNA cell, a medium such as a Dulbecco's modified Eagle's minimum essential medium (DMEM) with a serum component such as fetal bovine serum (FBS) and G418 may be used.

(2) The Method for Screening an Agent for Treating Diabetes

It is possible to screen a substance capable of controlling activities of the polypeptide for a screening tool (particularly a substance activating the polypeptide for a screening tool, i.e., agonist), using the polypeptide for a screening tool or the transformant for a screening tool. As described above, the polypeptide for a screening tool has an activity of promoting insulin secretion from pancreatic β cells by activation in the pancreatic β cells under a high glucose concentration. Therefore, a substance activating the polypeptide for a screening tool is useful as an active ingredient of an agent for promoting insulin secretion, capable of promoting insulin secretion from pancreatic β cells under a high glucose concentration, or as that of an agent for treating diabetes. Further, the polypeptide for a screening tool per se or the transformant for a screening tool per se may be used as a tool for screening an agent for treating diabetes (particularly an agent for promoting insulin secretion, more particularly an agent for promoting insulin secretion specifically under a high glucose concentration).

The term "promoting insulin secretion specifically under a high glucose concentration" as used herein means a condition in which an amount of insulin secreted significantly increases with respect to a control group under a high glucose concentration, and in which an amount of insulin secretion increased under a high glucose concentration in a group treated with a test compound with respect to the control group is 1.5 times or more (preferably 3 times or more) than that of insulin secretion increased under a low glucose concentration, more preferably a condition in which an amount of insulin secreted does not significantly increase in the group treated with a test compound with respect to the control group under a low glucose concentration. It may be decided whether or not an amount of insulin secretion has significantly increased in the group treated with a test compound with respect to the control group, for example, by carrying out an experiment under the conditions described in Example 8 or 12 and using Student's t-test. When the amount of insulin secreted has increased in the group treated with a test compound and the significant difference thereof with respect to the control group is p<0.05 (preferably p<0.01), it is decided that the amount of insulin secreted has significantly increased.

Compounds to be tested which may be screened using the screening tool of the present invention for an agent for treating diabetes are not particularly limited, but there may be mentioned, for example, various known compounds (including peptides) registered in chemical files, compounds obtained by combinatorial chemistry techniques (Terrett, N. K. et al., Tetrahedron, 51, 8135-8137, 1995), or random peptides prepared by employing a phage display method (Felici, F. et al., J. Mol. Biol., 222, 301-310, 1991) or the like. In addition, culture supernatants of microorganisms, natural components derived from plants or marine organisms, or animal tissue extracts may be used as the test compounds for screening. Further, compounds (including peptides) obtained by chemically or biologically modifying compounds (including peptides) selected by the screening tool of the present invention for an agent for treating diabetes may be used.

The screening method of the present invention for an agent for treating diabetes (preferably an agent for promoting insulin secretion, more preferably an agent for promoting insulin secretion specifically under a high glucose concentration) is not particularly limited, so long as it comprises the steps of bringing the transformant for a screening tool in which the polypeptide for a screening tool is expressed and functions as a receptor, or a cell membrane thereof, into contact with a compound to be tested and analyzing whether or not the polypeptide is activated. There may be mentioned, on the basis of differences in methods used for analyzing an activation of the polypeptide, for example, 1) a screening method in which changes of an intracellular cAMP concentration are used as an indicator (hereinafter referred to as "cAMP-type screening method"),
2) a screening method using a GTPγS binding method (hereinafter referred to as "GTPγS binding-type screening method"), or
3) a screening method using a ligand binding assay method (hereinafter referred to as "ligand binding-type screening method").

1) cAMP-type Screening Method

In the case of screening a substance activating the polypeptide for a screening tool (i.e., agonist) which is useful as an active ingredient of an agent for treating diabetes (particularly an agent for promoting insulin secretion, more particularly an agent for promoting insulin secretion specifically under a high glucose concentration) by the use of changes of an intracellular cAMP concentration as an indicator, it is analyzed whether or not the polypeptide is activated by bringing the transformant for a screening tool into contact with a test compound and analyzing (i.e., measuring or detecting) changes of the intracellular cAMP concentration in the cells, directly or indirectly. Namely, the cAMP-type screening method of the present invention in which changes of the intracellular cAMP concentration are used as an indicator comprises the steps of bringing the transformant for a screening tool into contact with a test compound and analyzing changes of the intracellular cAMP concentration in the cells. More particularly, the screening is preferably carried out by each method described in Example 6, 7, 10, or 11. For example, an increase in the intracellular cAMP concentration, as an indicator, is measured by exposing a test compound for a predetermined time, and then a test compound of which $EC_{50}$ is 10 µM or less (preferably 1 µM or less) may be selected as a substance having an agonist activity.

Changes of the intracellular cAMP concentration may be, for example, directly analyzed by use of a commercially available a cAMP measuring kit (Amersham or the like) as shown in Example 6 or 11, or indirectly analyzed by analyzing a transcriptional activity of a gene in which a regulation of the transcription is dependent on the cAMP concentration [such as a gene obtained by introducing a cAMP responsive element (CRE) upstream of a luciferase gene] as shown in Example 7 or 10.

When the transformant for a screening tool is brought into contact with a test compound, and then the intracellular cAMP concentration therein increases, it may be decided that the test compound is an agonist against the polypeptide for a screening tool. In this connection, the similar procedure is carried out using, as a control, a host cell not expressing the polypeptide for a screening tool or a cell transformed with empty vector instead of the transformant for a screening tool, and it is preferable to confirm that the cAMP concentration in the control cells is not increased by the test compound.

The screening for a substance activating the polypeptide for a screening tool by directly analyzing changes of the cAMP concentration using a commercially available cAMP measuring kit (Amersham or the like) may be carried out by, for example, the following procedure as shown in Example 6. More particularly, cells containing a gene encoding the polypeptide for a screening tool are cultured for 20 hours after the gene transfer, and the medium is removed. After 400 µL of 1 mmol/L IBMX (3-isobutyl-1-methylxanthine)/DMEM is added, the whole is incubated at 37° C. for 10 minutes in the presence of 5% $CO_2$. Further, a test compound (such as a compound, a peptide, or an antibody) diluted with 100 µL of 1 mmol/L IBMX/DMEM is added and further incubated for 30 minutes. The medium is removed, and then an amount of cAMP in the resulting cells is measured using a commercially available cAMP measuring kit (such as cAMP enzymeimmunoassay system; Amersham pharmacia biotech). A test compound in which a specific increase of the cAMP in the presence of the test compound is observed may be screened as a substance activating the polypeptide for a screening tool, i.e., an agent for treating diabetes.

The screening for a substance activating the polypeptide for a screening tool by indirectly analyzing changes of the cAMP concentration by analyzing a transcriptional activity of a gene in which a regulation of transcription is dependent on the cAMP concentration may be carried out by, for example, the following procedure as shown in Example 7. More particularly, cells containing a gene encoding the polypeptide for a screening tool and a gene in which a regulation of transcription is dependent on the cAMP concentration [for example, a gene obtained by introducing a cAMP responsive element (CRE) upstream of a luciferase gene; such as a pCRE-Luc vector (CLONTECH)] are cultured for 18 to 20 hours after the gene transfer. A test compound diluted with a medium is added and the whole is incubated at 37° C. for 5 to 6 hours in the presence of 5% $CO_2$. The medium is removed, and the cells are lysed with a cell lysing solution. A luciferase activity of the lysate is measured. A substance or the like in which a specific increase of a reporter activity in the presence of the test compound is observed may be screened as a substance activating the polypeptide for a screening tool, i.e., an agent for treating diabetes.

2) GTPγS Binding-type Screening Method

The screening for a substance activating the polypeptide for a screening tool (i.e., agonist) which is useful as an active ingredient of an agent for treating diabetes (particularly an agent for promoting insulin secretion, more particularly an agent for promoting insulin secretion specifically under a high glucose concentration) using a GTPγS binding method (Lazareno, S. and Birdsall, N. J. M., Br. J. Pharmacol., 109, 1120-1127, 1993) may be carried out by, for example, the following procedure. More particularly, a cell membrane expressing the polypeptide for a screening tool is mixed with $^{35}S$ labeled GTPγS (400 pmol/L) in a mixing solution [20 mmol/L HEPES (pH 7.4), 100 mmol/L NaCl, 10 mmol/L $MgCl_2$, and 50 mmol/L GDP]. After incubation in the presence or absence of a test compound, reaction solutions are filtered with a glass filter or the like, and then the remaining GTPγS radioactivity on each filter is measured by a liquid scintillation counter or the like. An agonist against the polypeptide for a screening tool, i.e., an agent for treating diabetes may be screened by a specific increase of the GTPγS binding in the presence of a test compound as an indicator.

The GTPγS binding-type screening method of the present invention using the GTPγS binding method comprises the steps of bringing a cell membrane of the transformant for a screening tool into contact with a test compound in the presence of 35S labeled GTPγS, separating the GTPγS binding to the cell membrane from the unbound GTPγS, and analyzing a radioactivity of one of the separated GTPγSs.

3) Ligand Binding-type Screening Method

The screening for a substance binding to the polypeptide for a screening tool which is useful as an active ingredient of an agent for treating diabetes (particularly an agent for promoting insulin secretion, more particularly an agent for promoting insulin secretion specifically under a high glucose concentration) using a ligand binding assay method may be carried out by, for example, the following procedure. More particularly, the transformant for a screening tool expressing the polypeptide for a screening tool, or a cell membrane thereof, or the polypeptide for a screening tool (preferably a purified preparation thereof) is prepared. Assay conditions such as a buffer, ions, and/or pH are optimized. The transformant expressing the polypeptide, or the cell membrane thereof, or the polypeptide, and a labeled substance obtained by, for example, the cAMP-type screening method and/or the GTPγS binding-type screening method [i.e., an agonist; such as 2-(pyridine-4-yl)ethyl thiobenzoate or L-α-lysophosphatidylcholine oleoyl] are incubated in the optimized buffer, together with a test compound, for a predetermined time. After the reaction, the whole is filtered with a glass filter or the like, and the filter is washed with an appropriate volume of the buffer. The remaining radioactivity on the filter is measured by a liquid scintillation counter or the like. A ligand of the polypeptide for a screening tool may be selected by the binding inhibition of the label as an indicator. In this connection, it may be confirmed that the ligand is an agonist or an antagonist by, for example, the cAMP-type screening method and/or the GTPγS binding-type screening method.

(3) The Pharmaceutical Composition for Treating Diabetes

The present invention includes a pharmaceutical composition comprising as an active ingredient a substance [for example, DNAs, proteins (including antibodies and fragments thereof), peptides, or other compounds] activating the polypeptide for a screening tool, for example, selected by the screening method of the present invention. The pharmaceutical composition of the present invention is preferably a pharmaceutical composition for treating and/or preventing diabetes (an agent for treating and/or preventing diabetes; more preferably a pharmaceutical composition for promoting insulin secretion, most preferably a pharmaceutical composition for promoting insulin secretion specifically under a high glucose concentration) comprising as an active ingredient a substance activating the polypeptide for a screening tool.

Further, the present invention includes a process for manufacturing a pharmaceutical composition for treating diabetes consisting of the steps of:

performing an analysis as described below in a quality control test of a pharmaceutical composition for treating diabetes; and preparing a formulation containing the analyzed substance.

The analysis may be carried out by (1) bringing a cell for a screening tool or a cell membrane thereof into contact with a test compound, and analyzing whether or not a polypeptide for a screening tool is activated; or (2) bringing a cell for a screening tool or a cell membrane thereof into contact with a test compound in the presence of a labeled agonist of a polypeptide for a screening tool, and analyzing a change of an amount of the labeled agonist which binds to the cell or the cell membrane thereof.

Further, the present invention includes a process for manufacturing a pharmaceutical composition for treating diabetes consisting of the step of preparing a formulation containing a substance obtained the screening method of the present invention comprising the analysis by the above-mentioned procedures.

As an active ingredient in the pharmaceutical composition of the present invention, a substance activating the polypeptide for a screening tool may be used. The activating substance may be selected by, for example, the screening method of the present invention. As the substance activating the polypeptide for a screening tool, there may be mentioned, for example, 2-(pyridine-4-yl)ethyl thiobenzoate (see Example 7) or L-α-lysophosphatidylcholine oleoyl (see Example 10), and 2-(pyridine-4-yl)ethyl thiobenzoate is preferable. The pharmaceutical composition of the present invention is not limited to a pharmaceutical composition comprising as an active ingredient a substance obtained by the screening method of the present invention, but includes a pharmaceutical composition comprising as an active ingredient a substance activating the polypeptide for a screening tool. As the pharmaceutical composition of the present invention, a pharmaceutical composition for promoting insulin secretion is preferable, and a pharmaceutical composition for promoting insulin secretion specifically under a high glucose concentration is more preferable.

In this connection, it is possible to confirm that a substance is effective in the treatment of diabetes by methods known to those skilled in the art or modified methods. For example, an activity of insulin secretion may be confirmed by a method described in Example 8. An activity of increasing an amount of insulin in plasma or an activity of decreasing blood glucose may be confirmed by, for example, a method described in Example 9.

The preparation comprising as an active ingredient a substance [for example, DNAs, proteins (including antibodies and fragments thereof), peptides, or other compounds] activating the polypeptide for a screening tool may be prepared, as a pharmaceutical composition, using pharmaceutically acceptable carriers, fillers, and/or other additives generally used in the preparation of formulation, in accordance with the active ingredient. The pharmaceutical composition of the present invention is preferably a pharmaceutical composition for treating and/or preventing diabetes comprising as an active ingredient a substance activating the polypeptide for a screening tool and promoting insulin secretion, more preferably a pharmaceutical composition for treating and/or preventing diabetes comprising as an active ingredient a substance activating the polypeptide for a screening tool and promoting insulin secretion specifically under a high glucose concentration. The present invention includes a method for treating and/or preventing diabetes comprising administering a substance activating the polypeptide for a screening tool.

Examples of administration include oral administration by tablets, pills, capsules, granules, fine granules, powders, oral solutions and the like, and parenteral administration by injections (e.g., intravenous, intramuscular, or the like), suppositories, transdermal preparations, transmucosal absorption preparations and the like. Particularly, in the case of peptides which are digested in the stomach, a parenteral administration such as an intravenous injection or the like is preferable.

In the solid composition for use in the oral administration, one or more active substances may be mixed with at least one inert diluent such as lactose, mannitol, glucose, microcrystalline cellulose, hydroxypropylcellulose, starch, polyvinyl pyrrolidone, or aluminum magnesium silicate. In the usual way, the composition may contain additives other than the inert diluent, such as a lubricant, a disintegrating agent, a stabilizing agent, or a solubilizing or solubilization assisting agent. If necessary, tablets or pills may be coated with a sugar coating or a film of a gastric or enteric substance.

The liquid composition for oral administration may include, for example, emulsions, solutions, suspensions, syrups, and elixirs, and may contain a generally used inert diluent such as purified water or ethyl alcohol. The composition may contain other additives other than the inert diluent such as moistening agents, suspending agents, sweeteners, flavors, or antiseptics.

The injections for parenteral administration may include aseptic aqueous or non-aqueous solutions, suspensions, and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil), alcohols (e.g., ethanol), polysorbate 80 and the like. Such a composition may further contain a moistening agent, an emulsifying agent, a dispersing agent, a stabilizing agent, a solubilizing or solubilization assisting agent, an antiseptic or the like. These compositions may be sterilized, for example, by filtration through a bacteria retaining filter, blending of a germicide, or irradiation. Alternatively, they may be used by first making into sterile solid compositions and dissolving them in sterile water or other sterile solvent for injection use prior to their use.

The dose is optionally decided by taking into consideration strength of each active ingredient, or symptoms, age, sex, or the like of each patient to be administered.

For example, in the case of oral administration, the usual dosage for an adult (60 kg in weight) is about 0.1 to 100 mg, preferably 0.1 to 50 mg per day. In the case of parenteral administration, the usual dosage is about 0.01 to 50 mg, preferably 0.01 to 10 mg per day in the form of an injection.

The polynucleotide encoding the polypeptide for a screening tool may be used for manufacturing the screening tool of the present invention as described above, and in addition is useful for a gene therapy.

For example, in a gene therapy using the polynucleotide encoding the polypeptide for a screening tool, the polypeptide for a screening tool is specifically overexpressed in pancreas, by specifically introducing the polynucleotide into pancreas. The polypeptide is spontaneously activated in the absence of the ligand, and promotes insulin secretion under a high glucose concentration. Therefore, the method is useful for treating diabetes. The gene therapy may be carried out in accordance with methods described in, for example, Japan Society of Gene Therapy, "Idenshi chiryou kaihatsu kenkyuu handobukku (Handbook of gene therapy research)", NTS, 1999, or Tadashi Ariga and Yukio Sakiyama, Tanpakushitsu Kakusan Koso, 40(17), 2772-2780, 1995.

Further, a substance promoting an expression of the polypeptide (particularly a natural polypeptide such as a polypeptide having the amino acid sequence of SEQ ID NO: 2 or 16) for a screening tool (such as a substance promoting a transcriptional activity of a polynucleotide encoding the polypeptide for a screening tool) may promote insulin secretion under a high glucose concentration by overexpressing the polypeptide for a screening tool, and thus is useful as an active ingredient of an agent for treating diabetes (particularly an agent for promoting insulin secretion, more particularly an agent for promoting insulin secretion specifically under a high glucose concentration). The expression-promoting substance may be selected, for example, by preparing an expression vector obtained by fusing a promoter region of a polynucleotide encoding the polypeptide for a screening tool upstream of an appropriate reporter gene (such as a luciferase gene), bringing cells transformed with the expression vector into contact with a test compound, and analyzing changes of expression of the reporter gene.

EXAMPLES

The present invention now will be further illustrated by, but is by no means limited to, the following Examples. The procedures were performed in accordance with the known methods (Maniatis, T., et al., "Molecular Cloning—A Laboratory Manual", Cold Spring Harbor Laboratory, NY, 1982), unless otherwise specified.

Example 1

Isolation of Polynucleotide Encoding Polypeptide Consisting of Amino Acid Sequence of SEQ ID NO: 2

A full-length cDNA encoding the polypeptide consisting of the amino acid sequence of SEQ ID NO: 2 was prepared by a reverse transcriptase-polymerase chain reaction (RT-PCR), using a human genomic DNA (TOYOBO) as a template, in accordance with the following procedures.

An oligonucleotide consisting of a nucleotide sequence of SEQ ID NO: 3 was used as a forward primer, and an oligonucleotide consisting of a nucleotide sequence of SEQ ID NO: 4 was used as a reverse primer. At each of the 5'-termini of the primers, an XbaI recognition sequence added thereto existed, respectively. The RT-PCR was carried out, using a polymerase (Pyrobest DNA polymerase; Takara-shuzo) in the presence of 5% dimethylsulfoxide (DMSO), by repeating a cycle composed of treatments at 98° C. for 10 seconds, at 58° C. for 30 seconds, and at 72° C. for 2 minutes, 34 times. As a result, a DNA fragment having about 1.0 kbp was amplified.

The resulting fragment was digested with a restriction enzyme, XbaI, and the resulting product was cloned in a pEF-BOS plasmid and a pEF-BOS signal sequence flag plasmid (Mizushima, S. and Nagata, S., Nucleic Acids Res., 18, 5322, 1990). A nucleotide sequence of a resulting clone was determined, using a DNA sequencer (ABI377 DNA Sequencer; Applied Biosystems) by a dideoxy terminator method, to find a nucleotide sequence of SEQ ID NO: 1.

To determine the 5'-terminus and 3'-terminus of cDNA coding the polypeptide consisting of the amino acid sequence of SEQ ID NO: 2, a RACE (rapid amplification of cDNA ends) method was carried out, using a human pancreas cDNA (Human Pancreas Marathon-Ready cDNA; Clontech) as a template. Procedures were concretely conducted in accordance with a manual attached to the above cDNA.

In a first PCR of the 5'-RACE, an oligonucleotide consisting of a nucleotide sequence of SEQ ID NO: 5 and an AP1 primer attached to the above cDNA were used; and in a second PCR, an oligonucleotide consisting of a nucleotide sequence of SEQ ID NO: 6 and an AP2 primer attached to the above cDNA were used. In a first PCR of the 3'-RACE, an oligonucleotide consisting of a nucleotide sequence of SEQ ID NO: 7 and the AP1 primer were used; and in a second PCR, an oligonucleotide consisting of a nucleotide sequence of SEQ ID NO: 8 and the AP2 primer were used.

The first PCR of each of the 5'-RACE and the 3'-RACE was carried out, using a Taq polymerase (LA Taq; Clontech), by repeating a cycle composed of treatments at 98° C. for 20 seconds, at 64° C. for 30 seconds, and at 72° C. for 3 minutes, 27 times. The second PCR was carried out, using a Taq polymerase (LA Taq; Clontech), by repeating a cycle composed of treatments at 98° C. for 20 seconds, at 64° C. for 30 seconds, and at 72° C. for 3 minutes, 34 times. Nucleotide sequences of resulting PCR products were determined by a DNA sequencer (ABI377 DNA Sequencer; Applied Biosystems) in accordance with a dideoxyterminator method.

From the 5'-RACE, a nucleotide sequence of SEQ ID NO: 9 was obtained as the sequence of 5'-terminus, and from the 3'-RACE, a nucleotide sequence of SEQ ID NO: 10 was obtained as the sequence of 3'-terminus. In the nucleotide sequence of SEQ ID NO: 9, a termination codon (tag; 161st-163rd) existed immediately upstream of a deduced initiation codon (atg; 200th-202nd), and between the above termination codon and the initiation codon, an initiation codon in frame did not exist. In the nucleotide sequence of SEQ ID NO: 10, a termination codon (taa; 217th-219th) existed at an expected position. Therefore, it was manifested that the nucleotide sequence of SEQ ID NO: 1 was a nucleotide sequence encoding a full-length amino acid sequence containing the initiation codon and the termination codon. Further, the amino acid sequence (335 amino acids) deduced from the above sequence corresponded to the amino acid sequence of SEQ ID NO: 2. The deduced amino acid sequence contained hydrophobic regions, which were supposed to be seven transmembrane domains, i.e., a characteristic feature of a G-protein coupled receptor. Therefore, it was manifested that the nucleotide sequence of SEQ ID NO: 1 encodes a G-protein coupled receptor.

Example 2

Confirmation of Expression Distribution of mRNA of Polypeptide Consisting of Amino Acid Ssequence of SEQ ID NO: 2

An expression distribution of the polynucleotide encoding the polypeptide consisting of the amino acid sequence of SEQ ID NO: 2 was analyzed by an RT-PCR method in accordance with the following procedures.

In a first step, a poly A+RNA (5 µg; Clontech) prepared from human organs, more particularly, brain, i.e., amygdala, caudate nucleus, hippocampus, corpus callosum, substantia nigra, and cerebellum, spinal cord, pituitary gland, heart, placenta, lung, trachea, liver, kidney, pancreas, small intestine, stomach, spleen, bone marrow, thymus, thyloid gland, salivary gland, adrenal gland, mammary gland, prostate, testis, and ovary, was reacted with a DNase (DNase; Nippon Gene) at 37° C. for 15 minutes. A part (4 µg) of a resulting poly A+RNA treated with the DNase was used for a reaction with a reverse transcriptase (MMLV Reverse Transcriptase; Clontech) at 42° C. for 60 minutes and 94° C. for 5 minutes, to obtain a cDNA. The resulting cDNA was dissolved in 800 µL of sterilized water.

The expression distribution of mRNA of the polypeptide consisting of amino acid sequence of SEQ ID NO: 2 was analyzed by a PCR wherein the resulting cDNAs from the above human organs were used as a template, and an oligonucleotide consisting of a nucleotide sequence of SEQ ID NO: 11 and an oligonucleotide consisting of a nucleotide sequence of SEQ ID NO: 12 were used as a primer set. The PCR was carried out, using a Taq polymerase (Ex Taq; Takara-shuzo). In the PCR, a cycle composed of treatments at 94° C. for 30 seconds, at 50° C. for 30 seconds, and at 72° C. for 1 minute was repeated 30 times in the presence of 5% DMSO. As an internal standard, a gene of human glyceraldehyde-3-phosphate dehydrogenase (G3PDH) was amplified by a PCR under the same conditions, using the cDNAs from the above human organs as a template, and a human G3PDH control amplimer set (Human G3PDH Control Amplimer Set; Clontech). Resulting PCR products were analyzed by an electrophoresis on 1% agalose gel. An amplified product having about 500 bp and obtained from mRNA of the polypeptide consisting of the amino acid sequence of SEQ ID NO: 2 was found only in a pancreas.

Example 3

Isolation and Confirmation of Expression Distribution of Rat Polynucleotide Corresponding to that Encoding Polypeptide Consisting of Amino Acid Sequence of SEQ ID NO: 2

A rat polynucleotide corresponding to the human polynucleotide encoding the polypeptide consisting of the amino acid sequence of SEQ ID NO: 2 and isolated in Example 1 was obtained by the following procedures.

A PCR was first carried out, using a rat genomic DNA (rat genomic DNA; Clontech) as a template and the oligonucleotide consisting of the nucleotide sequence of SEQ ID NO: 11 and the oligonucleotide consisting of the nucleotide sequence of SEQ ID NO: 12, each used in Example 2, as a primer set. In the PCR, a DNA polymerase (Pyrobest DNA polymerase;. Takara-shuzo) was used, and a cycle composed of treatments at 98° C. for 10 seconds, at 57° C. for 30 seconds, and at 72° C. for 1 minute was repeated 34 times in the presence of 5% DMSO. Then, a further PCR was carried out, using resulting PCR products as a template. In the PCR, a DNA polymerase (Pyrobest DNA polymerase; Takara-shuzo) was used, and a cycle composed of treatments at 98° C. for 10 seconds, at 55° C. for 30 seconds, and at 72° C. for 1 minute was repeated 34 times in the presence of 5% DMSO. Partial sequences of resulting PCR fragments were analyzed, and four oligonucleotides consisting of nucleotide sequences of SEQ ID NO: 21 to NO: 24 were designed as primers for a RACE method.

In the following RACE method, a brain cDNA (Marathon-Ready cDNA; Clontech) was used as a template. For the 5'-RACE, the oligonucleotide consisting of the nucleotide sequence of SEQ ID NO: 21 and an AP1 primer (attached to the above cDNA) were used in a first PCR; and the oligonucleotide consisting of the nucleotide sequence of SEQ ID NO: 22 and an AP2 primer (attached to the above cDNA) were used in a second PCR. For the 3'-RACE, the oligonucleotide consisting of the nucleotide sequence of SEQ ID NO: 23 and the above AP1 primer were used in a first PCR; and the oligonucleotide consisting of the nucleotide sequence of SEQ ID NO: 24 and the above AP2 primer were used in a second PCR.

In each of the first and second PCRs of the 5'-RACE, a Taq polymerase (LA Taq; Clontech) was used, and a cycle composed of treatments at 98° C. for 20 seconds, at 65° C. for 30 seconds, and at 72° C. for 3 minutes was repeated 34 times, respectively. In each of the first and second PCRs of the 3'-RACE, a Taq polymerase (LA Taq; Clontech) was used, and a cycle composed of treatments at 98° C. for 20 seconds, at 65° C. for 30 seconds, and at 72° C. for 5 minutes was repeated 34 times, respectively. Nucleotide sequences of resulting PCR products of the 5'-RACE and the 3'-RACE were analyzed.

An oligonucleotide consisting of a nucleotide sequence of SEQ ID NO: 25 and an oligonucleotide consisting of a nucleotide sequence of SEQ ID NO: 26 were designed on the basis of the determined nucleotide sequences. A PCR was carried out, using the designed primer set and the rat brain cDNA as a template. In the PCR, a DNA polymerase (pfu turbo DNA polymerase; STRATAGENE) was used; and a cycle composed of treatments at 98° C. for 20 seconds, at 64° C. for 30 seconds, and at 74° C. for 2 minutes was repeated 12 times, a cycle composed of treatments at 98° C. for 20 seconds, at 61° C. for 30 seconds, and at 74° C. for 2 minutes was repeated 12 times, and a cycle composed of treatments at 98° C. for 20 seconds, at 58° C. for 30 seconds, and at 74° C. for 2 minutes was repeated 16 times. Then, a further PCR was carried out, using resulting PCR products as a template. In the PCR, a DNA polymerase (pfu turbo DNA polymerase; STRATAGENE) was used; and a cycle composed of treatments at 98° C. for 20 seconds, at 64° C. for 30 seconds, and at 74° C. for 150 seconds was repeated 12 times, a cycle composed of treatments at 98° C. for 20 seconds, at 61° C. for 30 seconds, and at 74° C. for 150 seconds was repeated 12 times, and a cycle composed of treatments at 98° C. for 20 seconds, at 58° C. for 30 seconds, and at 74° C. for 150 seconds was repeated 16 times. Resulting PCR products (hereinafter referred to as PCR products A) were subcloned and nucleotide sequences thereof were confirmed.

Subsequently, an oligonucleotide consisting of a nucleotide sequence of SEQ ID NO: 13 (a forward primer) and an oligonucleotide consisting of a nucleotide sequence of SEQ ID NO: 14 (a reverse primer) were designed on the basis of the determined nucleotide sequences. There existed an XbaI recognition sequence added at 5'-terminus of each of the primers, respectively. A PCR was carried out, using the primer set and the subcloned PCR products A as a template. In the PCR, a DNA polymerase (pfu turbo DNA polymerase; STRAT- AGENE) was used, and a cycle composed of treatments at 98° C. for 20 seconds, at 59° C. for 30 seconds, and at 74° C. for 90 seconds was repeated 25 times. As a result, a DNA fragment having about 1.0 kbp was amplified. The resulting fragment was digested with a restriction enzyme, XbaI, and then cloned into a pEF-BOS plasmid. A nucleotide sequence of a resulting clone was determined, using a DNA sequencer (ABI377 DNA Sequencer; Applied Biosystems) by a dideoxy terminator method, to find a nucleotide sequence of SEQ ID NO: 15. An amino acid sequence deduced from the resulting nucleotide sequence was an amino acid sequence of SEQ ID NO: 16.

Thereafter, a PCR was carried out, using an oligonucleotide consisting of a nucleotide sequence of SEQ ID NO: 17 and an oligonucleotide consisting of a nucleotide sequence of SEQ ID NO: 18, each designed on the basis of the resulting nucleotide sequences, as a primer set, and cDNA prepared from a rat pancreatic β cell line RIN-5F (ATCC: CRL-2058) as a template. The cDNA used was synthesized by preparing a total RNA using a total RNA purifying reagent (ISOGEN; NIPPONGENE), and then, reacting with a reverse transcriptase. In the PCR, a Taq polymerase (rTaq; Takara-shuzo) was used, and a cycle composed of treatments at 94° C. for 30 seconds, at 57° C. for 30 seconds, and at 72° C. for 1 minute was repeated 34 times, in the presence of 5% DMSO. Resulting PCR products were analyzed by an electrophoresis on 1% agalose gel. It was confirmed that mRNA of the polypeptide consisting of the amino acid sequence of SEQ ID NO: 16 was expressed in the rat pancreatic β cell line.

Further, a PCR was carried out for the cDNA prepared from a mouse pancreatic β cell line NIT-1 (ATCC: CRL-2055). The cDNA used was synthesized, as in the case of the above rat pancreatic β cell line RIN-5F, by preparing a total RNA using a total RNA purifying reagent (ISOGEN; NIPPONGENE), and then reacting with a reverse transcriptase. The PCR was carried out by repeating the procedures described in the case of the above rat pancreatic β cell line RIN-5F, except that an oligonucleotide consisting of a nucleotide sequence of SEQ ID NO: 19 and an oligonucleotide consisting of a nucleotide sequence of SEQ ID NO: 20, each designed on the basis of the nucleotide sequence of the above rat polypeptide, i.e., the nucleotide sequence of SEQ ID NO: 15, were used as a primer set, to find a DNA fragment having about 400 bp. It was presumed that the resulting DNA fragment was a part of a mouse polynucleotide corresponding to the human polynucleotide consisting of the nucleotide sequence of SEQ ID NO: 1 or the rat polynucleotide consisting of the nucleotide sequence of SEQ ID NO: 15. Further, it was confirmed that mRNA of the mouse polynucleotide corresponding to the polynucleotide encoding the polypeptide consisting of the amino acid sequence of SEQ ID NO: 2 or NO: 16 was also expressed in the mouse pancreatic β cell line.

The results of Example 2 and the present Example showed that the mRNA of the polynucleotide encoding the polypeptide consisting of the amino acid sequence of SEQ ID NO: 2, or the corresponding rat or mouse polynucleotide was expressed specifically in a pancreas, an organ deeply involved with diabetes, and in the pancreatic β cell lines. Therefore, it would be possible to use a pancreatic β cell line or a pancreas cell for a selection of substances which may activate the polypeptide consisting of the amino acid sequence of SEQ ID NO: 2 or the like, instead of the expression of the polynucleotide encoding the polypeptide consisting of the amino acid sequence of SEQ ID NO: 2, or the corresponding rat or mouse polynucleotide by an introduction thereof into various cell strains.

Example 4

Expression of Polypeptide Consisting of Amino Acid Sequence of SEQ ID NO: 2 in 293-EBNA Cell and Change of Intracellular cAMP Concentration by Overexpression To express the polypeptide consisting of the amino acid sequence of SEQ ID NO: 2, the clone prepared in Example 1, i.e., the pEF-BOS signal sequence flag plasmid containing the full-length cDNA encoding the polypeptide consisting of the amino acid sequence of SEQ ID NO: 2 (hereinafter referred to as plasmid pEF-BOS SSF-NA), was used. This was because the expression vector capable of adding a signal sequence to the N-terminus of the desired polypeptide was used to express the desired polypeptide at a high frequency on a cell membrane.

293-EBNA cells ($7 \times 10^4$ cells/well) were seeded on a 24-well plate coated with collagen, and cultured for 24 hours. Then, a transfection reagent (FuGENE6; Boeringer Mannheim) was used to transfect a plasmid pEF-BOS SSF-NA or a plasmid pEF-BOS (negative control vector) to the cells. The transfected cells were further cultured for 20 hours, and then a medium was aspirated. After adding 500 µL of 1 mmol/L IBMX (3-isobutyl-1-methylxanthine)/DMEM, the whole was incubated at 37° C. for 40 minutes in the presence of 5% $CO_2$. The IBMX used was a phosphodiesterase inhibitor. Then, the medium was aspirated, and an amount of cAMP of the resulting cells was measured. A commercially available cAMP enzymeimmunoassay system (Amersham Pharmacia Biotech) was used for the measurement of the amount of cAMP.

The results showed that the amount of the intracellular cAMP was increased dependent upon the amount of the plasmids, in the cells to which the plasmid pEF-BOS SSF-NA had been transfected, whereas no change in the amount of the intracellular cAMP was observed, in the cells to which the plasmid pEF-BOS had been transfected. The increase of the amount of cAMP by the overexpression of the polypeptide consisting of the amino acid sequence of SEQ ID NO: 2 showed that cAMP was one of the second messengers of the polypeptide consisting of the amino acid sequence of SEQ ID NO: 2.

Example 5

Expression of Polypeptide Consisting of Amino Acid Sequence of SEQ ID NO: 2 in Mouse Pancreatic β Cell Line NIT-1 and Change of Amount of Secreted Insulin by Overexpression The polypeptide consisting of the amino acid sequence of SEQ ID NO: 2 or NO: 16 was expressed specifically in a pancreas, and the expression thereof in pancreatic β cell lines was confirmed (see Examples 2 and 3). It would be possible to presume the function of the polypeptide by overexpressing the polypeptide in the pancreatic β cell lines. To express the polypeptide consisting of the amino acid sequence of. SEQ ID NO: 2, the plasmid pEF-BOS SSF-NA used in Example 4 was also used in the present Example.

NIT-1 Cells ($4 \times 10^5$ cells) were seeded on a 24-well plate, and cultured for 24 hours. Then, a transfection reagent (FuGENE6; Boeringer Mannheim) was used to transfect the plasmid pEF-BOS SSF-NA or the plasmid pEF-BOS (negative control vector) to the cells. The transfected cells were further cultured for 2 or 3 days, and then a medium was aspirated. After washing with a phosphate buffered saline (PBS), 1 mL of 3.3 mmol/L glucose-containing KRBB (Krebs-Ringer bicarbonate buffer) was added, and the whole was incubated at 37° C. for 1 or 2 hours, in the presence of 5% $CO_2$. Then, the buffer was aspirated, and 1 mL of 3.3 mmol/L glucose-containing KRBB or 1 mL of 16.8 mmol/L glucose-containing KRBB was added. The whole was incubated at 37° C. for 2 hours in the presence of 5% $CO_2$. An amount of insulin in supernatants was measured. A commercially available insulin radioimmunoassay kit (Phadeseph insulin; Pharmacia Upjohn) was used for the measurement of the amount of insulin secreted.

It was revealed that the overexpression of the polypeptide consisting of the amino acid sequence of SEQ ID NO: 2 did not cause a change of an amount of insulin secreted in the presence of 3.3 mmol/L glucose, but did cause an increase of an amount of insulin secreted in the presence of 16.8 mmol/L glucose.

The results showed that the polypeptide consisting of the amino acid sequence of SEQ ID NO: 2 was a G-protein coupled receptor expressed specifically in a pancreas as shown in Example 2, and exhibited a function to accelerate a secretion of insulin dependent upon a concentration of glucose. Therefore, it would be possible to prevent and/or treat a pancreatic disease, especially diabetes, by activating the polypeptide consisting of the amino acid sequence of SEQ ID NO: 2.

Example 6

Screening of Substances Capable of Modifying Activity of Polypeptide Consisting of Amino Acid Sequence of SEQ ID NO: 2, Based on Change of Intracellular cAMP Concentration—Part 1

To express the polypeptide consisting of the amino acid sequence of SEQ ID NO: 2, the clone prepared in Example 1, that is, the pEF-BOS plasmid to which the full-length cDNA encoding the polypeptide consisting of the amino acid sequence of SEQ ID NO: 2 had been introduced (hereinafter referred to as plasmid pEF-BOS-NA), was used.

293-EBNA Cells ($7 \times 10^4$ cells/well) were seeded on a 24-well plate coated with collagen, and cultured for 24 hours. Then, a transfection reagent (FuGENE6; Boeringer Mannheim) was used to transfect 50 ng of a plasmid pEF-BOS-NA or a plasmid pEF-BOS (negative control vector) to the cells. The transfected cells were further cultured for 20 hours, and then a medium was aspirated. After adding 400 μL of 1 mmol/L IBMX (3-isobutyl-1-methylxanthine)/DMEM, the whole was incubated at 37° C. for 10 minutes in the presence of 5% $CO_2$. Further, a test compound, such as a compound, peptide, or an antibody, diluted with 100 μL of 1 mmol/L IBMX was added, and the whole was incubated for 30 minutes. Then, the medium was aspirated, and resulting cells were used for a measurement of an amount of cAMP. A commercially available cAMP enzymeimmunoassay system (Amersham Pharmacia Biotech) can be used for the measurement of the amount of cAMP, and the test compound bringing about an increase of the amount of cAMP specifically in cells wherein the polypeptide consisting of the amino acid sequence of SEQ ID NO: 2 was expressed can be selected as a substance capable of activating the polypeptide consisting of the amino acid sequence of SEQ ID NO: 2.

Example 7

Screening of Substances Capable of Modifying Activity of Polypeptide Consisting of Amino Acid Sequence of SEQ ID NO: 2, Based on Change of Intracellular cAMP Concentration—Part 2

The pEF-BOS-NA plasmid used in Example 6 was also used in the present Example.

293-EBNA cells, ($1 \times 10^4$ cells/well) were seeded on a 96-well plate coated with collagen, and cultured overnight in a Dulbecco modified Eagles' medium (DMEM) containing 10% fetal calf serum (FCS). Then, a transfection reagent (LIPOFECTAMINE 2000; GIBCO BRL) was used to transfect 0.01 ng of a plasmid pEF-BOS-NA or a plasmid pEF-BOS (negative control vector) and 5 ng of a pCRE-Luc vector (CLONTECH) to the cells. The transfected cells were further cultured for 18-20 hours, and then a test compound (a known compound, but unknown to exhibit an efficacy for treating diabetes) diluted with the medium was added, and the whole was incubated at 37° C. for 5-6 hours in the presence of 5% $CO_2$. After the medium was aspirated, the cells were lysed with a cell lysing solution (cell lysis buffer LCβ; Toyo Ink Mfg.). A luciferase activity of the lysate was measured by a commercially available measuring kit (PicaGene Luminescent kit; Toyo Ink Mfg.) and a measuring apparatus (ML3000 microtiter plate luminometer; Dynatech Laboratories).

The test compounds bringing about an increase of a reporter activity specifically in cells wherein the polypeptide consisting of the amino acid sequence of SEQ ID NO: 2 was expressed were selected as a substance capable of enhancing an activity of the polypeptide consisting of the amino acid sequence of SEQ ID NO: 2, and four different compounds including 2-(pyridine-4-yl)ethyl thiobenzoate (LT-1 Z 0059519; LaboTest) could be obtained. An $EC_{50}$ value of 2-(pyridine-4-yl)ethyl thiobenzoate was 3.2 μM.

Example 8

Experiment of Secreting Insulin from Mouse Pancreatic β Cell Line MIN6—Part 1

MIN6 cells ($2 \times 10^5$ cells) were seeded on a 24-well plate, and cultured for 2 days in a DMEM containing 10% FCS. The medium was aspirated, and the cells were washed with KRB-HEPES (140 mmol/L NaCl, 3.6 mmol/L KCl, 0.5 mmol/L $NaH_2PO_4$, 0.5 mmol/L $MgSO_4$, 1.5 mmol/L $CaCl_2$, 10 mmol/L Hepes, 2 mmol/L $NaHCO_3$, 0.1% BSA, pH7.4). After 2.8 mmol/L glucose-containing KRB-HEPES (1 ml) was added, the whole was incubated at 37° C. for 30-60 minutes in the presence of 5% $CO_2$.

After the buffer was aspirated, one of the four compounds obtained by the screening in Example 7, i.e., 2-(pyridine-4-yl)ethyl thiobenzoate, in the form of a solution (0.5 ml) prepared by diluting the compound with 2.8 mmol/L or 16.8 mmol/L glucose-containing KRB-HEPES, was added, and the whole was incubated at 37° C. for 20 minutes in the presence of 5% $CO_2$. A supernatant was used for measuring an amount of insulin secreted.

A commercially available insulin radioimmunoassay kit (Phadeseph insulin; Pharmacia Upjohn) was used for the measurement of the amount of insulin secreted.

It was revealed that the stimulation by 2-(pyridine-4-yl) ethyl thiobenzoate did not cause an increase of an amount of insulin secreted in the presence of 2.8 mmol/L glucose, but caused an increase of an amount of insulin secreted in the presence of 16.8 mmol/L glucose. Therefore, it showed that 2-(pyridine-4-yl)ethyl thiobenzoate can exhibit a function to accelerate a secretion of insulin only when stimulated by. a high concentration of glucose.

For one of the three compounds found in Example 7, other than 2-(pyridine-4-yl)ethyl thiobenzoate, the procedures described for the experiment of 2-(pyridine-4-yl)ethyl thiobenzoate were repeated. It was revealed that the stimulation by the compound did not cause an increase of an amount of insulin secreted in the presence of 2.8 mmol/L glucose, but caused an increase of an amount of insulin secreted in the presence of 16.8 mmol/L glucose. Therefore, it showed that the compound can exhibit a function to accelerate a secretion of insulin only when stimulated by a high concentration of glucose.

Example 9

Glucose Tolerance Tests for SD Rats and GK Rats by One Oral Dose

SD rats (4 weeks old; CLEA JAPAN) were forced to fast overnight, and 2 g/kg of glucose was orally administered. 100 mg/kg of 2-(pyridine-4-yl)ethyl thiobenzoate (LT-1 Z 0059519) had been intraperitoneally administered 5 minutes before the glucose administration. An appropriate amount of blood was taken 0 minute, 30 minutes, 60 minutes, and 120 minutes after the glucose administration, and used for the measurement of a blood glucose level and a concentration of plasma insulin.

For measuring the blood glucose level, a supernatant obtained by mixing blood and 0.33 mol/L perchloric acid (blood:0.33 mol/L perchloric acid=1:10) and centrifuging the mixture (3000×g, 10 minutes, 4° C.) was used. For measuring the concentration of plasma insulin, a supernatant obtained by centrifuging blood (3000×g, 10 minutes, 4° C.) was used. Further, Glucose C test Wako (Wako) was used in the measurement of the blood glucose level, and a rat insulin assay system (Amersham) was used in the measurement of the concentration of plasma insulin.

Figure 2:
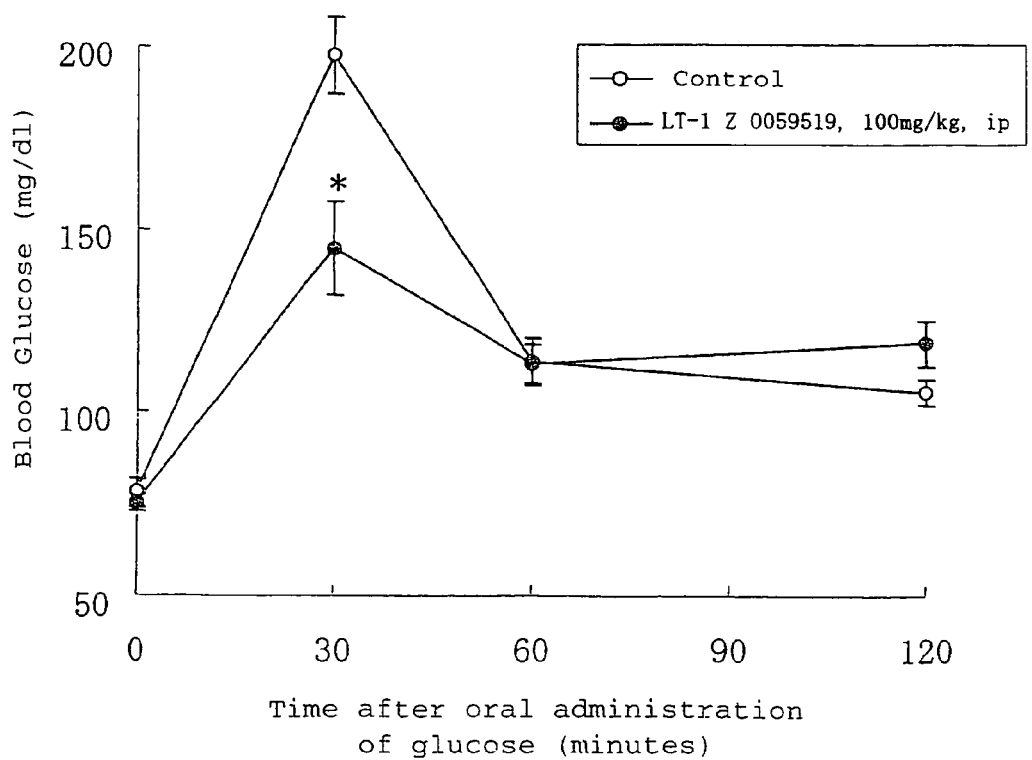
FIG. 2 is a graph showing a time course of the blood glucose level after the oral administration of glucose in SD rats to which 2-(pyridine-4-yl)ethyl thiobenzoate (LT-1 Z 0059519) was intraperitoneally administered.

The results are shown in FIGS. 1 and 2. FIG. 1 illustrates a time course of the concentration of plasma insulin (unit=ng/mL) after the oral administration of glucose, and FIG. 2 illustrates a time course of the blood glucose level (unit=mg/dL) after the oral administration of glucose. The mark "*" in FIGS. 1 and 2 denotes that a significant difference against the control group, i.e., the group to which no 2-(pyridine-4-yl) ethyl thiobenzoate had been administered, was $p<0.05$ (Student's t-test).

As shown in FIG. 1, a significant increase of the concentration of plasma insulin was observed at 30 minutes after glucose administration, in the group to which 100 mg/kg of 2-(pyridine-4-yl)ethyl thiobenzoate had been administered. Further, an increase of the blood glucose level by the glucose administration was significantly suppressed at 30 minutes after glucose administration, in the group to which 100 mg/kg of 2-(pyridine-4-yl)ethyl thiobenzoate had been administered.

Therefore, it was confirmed that, in the SD rats to which glucose was administered, 2-(pyridine-4-yl)ethyl thiobenzoate exhibited a function to increase the amount of insulin in plasma, and a function to reduce the blood glucose level.

Then, a glucose tolerance test for GK (Goto-Kakizaki) rats (type II diabetes models with incomplete insulin secretion; 7 weeks old; Charles River Japan) by one oral dose was carried out. The GK rat line was established by selectively mating wistar rats in accordance with an index of a poor tolerance in an oral glucose tolerance test, by Yoshio Goto, et al., School of Medicine, Tohoku University, in 1975.

The procedures of the glucose tolerance test for SD rats were repeated except that 2-(pyridine-4-yl)ethyl thiobenzoate was orally administered.

FIG. 3 illustrates a time course of the blood glucose level (unit=mg/dL) after the oral administration of glucose. In FIG. 3, the mark "*" denotes that a significant difference against the control group, i.e., the group to which no 2-(pyridine-4-yl)ethyl thiobenzoate had been administered, was $p<0.05$ (Student's t-test), and the mark "**" denotes that the significant difference as above was $p<0.01$.

As shown in FIG. 3, an increase of the blood glucose level by the glucose administration was significantly suppressed at 30 and 60 minutes after glucose administration, in the group to which 100 mg/kg of 2-(pyridine-4-yl)ethyl thiobenzoate had been administered, and therefore, the utility of 2-(pyridine-4-yl)ethyl thiobenzoate was confirmed in the diabetes model rat.

Example 10

Screening of Substances Capable of Modifying Activity of Polypeptide Consisting of Amino Acid Sequence of SEQ ID NO: 2, Based on Change of Intracellular cAMP Concentration—Part 3

The pEF-BOS-NA plasmid used in Example 6 was also used in the present Example.

293-EBNA cells ($7 \times 10^4$ cells/well) were seeded on a 24-well plate coated with collagen, and cultured overnight in a Dulbecco modified Eagles' medium (DMEM) containing 1% fetal calf serum (FCS). Then, a transfection reagent (LIPOFECTAMINE 2000; GIBCO BRL) was used to transfect 0.1 ng of a plasmid pEF-BOS-NA or a plasmid pEF-BOS (negative control vector) and 20 ng of a pCRE-Luc vector (CLONTECH) to the cells. The transfected cells were further cultured for 18-20 hours, and then a test compound diluted with a medium containing 0.1% BSA was added, and the whole was incubated at 37° C. for 6 hours in the presence of 5% $CO_2$. After the medium was aspirated, the cells were lysed with a cell lysing solution (cell lysis buffer LCβ; Toyo Ink Mfg.). A luciferase activity of the lysate was measured by a commercially available measuring kit (PicaGene Luminescence kit; Toyo Ink Mfg.) and a measuring apparatus (ML3000 microtiter plate luminometer; Dynatech Laboratories).

The test compounds bringing about an increase of a reporter activity specifically in cells wherein the polypeptide consisting of the amino acid sequence of SEQ ID NO: 2 was expressed were selected as a substance capable of enhancing an activity of the polypeptide consisting of the amino acid sequence of SEQ ID NO: 2. L-α-lysophosphatidylcholine oleoyl (L1881; SIGMA), a biocomponent, could be obtained.

Example 11

Screening of Substances Capable of Modifying Activity of Polypeptide Consisting of Amino Acid Sequence of SEQ ID NO: 2, Based on Change of Intracellular cAMP Concentration—Part 4

The pEF-BOS-NA plasmid used in Example 6 was also used in the present Example.

293-EBNA Cells (1×10⁴ cells/well) were seeded on a 96-well plate coated with collagen, and cultured for 24 hours. Then, a transfection reagent (LIPOFECTAMINE 2000; GIBCO BRL) was used to transfect 3 ng of a plasmid pEF-BOS-NA or a plasmid pEF-BOS (negative control vector) to the cells. The transfected cells were further cultured for 20 hours, and the medium was aspirated. After 80 μL of 1 mmol/L IBMX (3-isobutyl-1-methylxanthine)/0.1% BSA/DMEM was added, the whole was incubated at 37° C. for 10 minutes in the presence of 5% $CO_2$. Then, a test compound diluted with 20 μL of 1 mmol/L IBMX/0.1% BSA/DMEM was added, and the whole was incubated for 30 minutes. After the medium was aspirated, the resulting cells were used for the measurement of an amount of cAMP. A commercially available cAMP enzymeimmunoassay system (cyclic AMP kit; Nihon Schering) was used to measure the amount of cAMP. The compound selected in Example 10, i.e., L-α-lysophosphatidylcholine oleoyl, exhibited an increase of the amount of cAMP specifically in the cells wherein the polypeptide consisting of the amino acid sequence of SEQ ID NO: 2 was expressed, and therefore, selected as a substance capable of activating the polypeptide consisting of the amino acid sequence of SEQ ID NO: 2.

Example 12

Experiment of Secreting Insulin from Mouse Pancreatic β Cell Line MIN6—Part 2

MIN6 cells (2.5×10⁵ cells) were seeded on a 24-well plate coated with collagen, and cultured for 2 days in a DMEM containing 10% FCS (Cat. No. 11995-065; GIBCO BRL). The medium was aspirated, and 0.4 mL of a glucose-free DMEM containing 10% FCS (Cat. No. 11966-025; GIBCO BRL) was added. The whole was incubated at 37° C. for 2 hours in the presence of 5% $CO_2$.

After the medium was aspirated, 0.5 mL of a solution of L-α-lysophosphatidylcholine oleoyl, the compound selected by the screening method in Example 10, diluted with 2.8 mmol/L or 16.8 mmol/L glucose-containing DMEM (Cat. No. 11966-025; GIBCO BRL) was added, and the whole was incubated at 37° C. for 30 minutes in the presence of 5% $CO_2$. A supernatant was used for measuring an amount of insulin secreted.

A commercially available insulin radioimmunoassay kit (Phadeseph insulin; Pharmacia Upjohn) was used for the measurement of the amount of insulin secreted.

It was revealed that the stimulation by L-α-lysophosphatidylcholine oleoyl caused an increase of an amount of insulin secreted in the presence of 16.8 mmol/L glucose.

INDUSTRIAL APPLICABILITY

The polypeptide having the amino acid sequence of SEQ ID NO: 2 or 16, the variation functionally equivalent thereto, and the homologous polypeptide are pancreas-specific polypeptides and exhibit the activity of promoting insulin secretion under a high glucose concentration. Therefore, by use of these polypeptides, a convenient screening system for obtaining a substance useful as an agent for treating diabetes (particularly an agent for promoting insulin secretion, more particularly an agent for promoting insulin secretion specifically under a high glucose concentration) capable of controlling blood glucose within a normal range may be constructed.

Further, a pharmaceutical composition for treating diabetes (particularly a pharmaceutical composition for promoting insulin secretion, more particularly a pharmaceutical composition for promoting insulin secretion specifically under a high glucose concentration) comprising as an active ingredient an activating substance obtainable by the screening tool or screening method of the present invention and capable of controlling blood glucose within a normal range may be manufactured.

Furthermore, one of the screening tool of the present invention, the cell for the screening tool or the cell membrane thereof may be used not only for screening a substance useful as an agent for treating diabetes but also in a quality control test of a pharmaceutical composition for treating diabetes.

Free Text In Sequence Listing

Features of "Artificial Sequence" are described in the numeric identifier <223> in the Sequence Listing. More particular, each of the nucleotide sequences of SEQ ID NOS: 3, 4, 13, and 14 is an artificially synthesized primer sequence.

As above, the present invention is explained with reference to particular embodiments, but modifications and improvements obvious to those skilled in the art are included in the scope of the present invention.

The invention claimed is:

1. A method for screening an agent for treating diabetes, comprising:

bringing a cell which is transformed with an expression vector comprising at least one polynucleotide encoding at least one polypeptide and is expressing the at least one polypeptide, or a cell membrane thereof, into contact with an agent to be tested, wherein the at least one polypeptide is a polypeptide selected from the group consisting of SEQ ID NO.: 2 or 16;

analyzing whether or not the polypeptide is activated by the agent;

selecting an agent activating the polypeptide; and confirming that the selected agent exhibits an activity of increasing insulin secretion or an activity of increasing an amount of insulin in plasma.

2. A method for screening an agent for treating diabetes, comprising:

bringing a cell which is transformed with an expression vector comprising at least one polynucleotide encoding at least one polypeptide and is expressing the at least one polypeptide, a cell membrane thereof, or the at least one polypeptide, into contact with an agent to be tested, in the presence of a labeled agonist of the polypeptide, wherein the at least one polypeptide is selected from the group consisting of SEQ ID NO.: 2 or 16;

analyzing a change of an amount of the labeled agonist which binds to the cell, the cell membrane thereof, or the polypeptide; and confirming that the analyzed agent exhibits an activity of increasing insulin secretion or an activity of increasing an amount of insulin in plasma.

3. The method of claim 1, wherein the confirmation step is carried out under a high glucose concentration.

4. The method of claim 2, wherein the confirmation step is carried out under a high glucose concentration.

* * * * *

UNITED STATES PATENT AND TRADEMARK OFFICE
CERTIFICATE OF CORRECTION

| | | |
|---|---|---|
| PATENT NO. | : 7,662,775 B2 | Page 1 of 1 |
| APPLICATION NO. | : 10/975367 | |
| DATED | : February 16, 2010 | |
| INVENTOR(S) | : Ohishi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 241 days.

Signed and Sealed this

Twenty-sixth Day of October, 2010

David J. Kappos
*Director of the United States Patent and Trademark Office*